US006221594B1

(12) United States Patent
Burrell et al.

(10) Patent No.: US 6,221,594 B1
(45) Date of Patent: Apr. 24, 2001

(54) METHOD FOR THE DETECTION OF AQUATIC NITRITE OXIDIZING MICROORGANISMS OF THE GENUS NITROSPIRA

(75) Inventors: Paul Christopher Burrell, Orange; Linda Louise Blackall, Yeronga; Jurg Keller, Taringa, all of (AU)

(73) Assignee: CRC for Waste Management and Pollution Control Limited, New South Wales (AU)

( * ) Notice: Subject to any disclaimer, the term of this patent is extended or adjusted under 35 U.S.C. 154(b) by 0 days.

(21) Appl. No.: 09/193,377

(22) Filed: Nov. 17, 1998

(51) Int. Cl.[7] ............................... C12Q 1/68; C12Q 1/48; C12P 19/34; C07H 21/02; C07H 21/04

(52) U.S. Cl. ............................. 435/6; 435/15; 435/91.2; 435/194; 435/810; 536/23.1; 536/24.32; 536/24.33

(58) Field of Search ................... 435/6, 15, 91.2, 435/194, 810; 536/23.1, 24.32, 24.33

(56) References Cited

U.S. PATENT DOCUMENTS 5,811,269 * 9/1998 Nadeau et al. ...................... 435/91.1

OTHER PUBLICATIONS

Hovanec, T.A. et al. Applied and Environmental Microbiology 64(1):258–264, Jan. 1998.*
Teske, A. et al. J. Bacteriol. 176(21):6623–6630, Nov. 1994.*
Hiorns, W.D. et al. Microbiology 141:2793–2800, 1995.*
Amann, R.I. et al. Appl. Environ. Microbiol. 56(6):1919–1925, Jun. 1990.*
Erlich, H.A. et al. Science 252:1643–1650, Jun. 1991.*
Hovanec, T.A. et al. GenBank Accession No. AF035813, Jan. 1998.*
Juretschko, S. et al. GenBank Accession No. AF033559, Oct. 1998.*
Paul C. Burrell et al., *Microbiology of a Nitrite–Oxidizing Bioreacto , Applied and Environmental Microbiology*, vol. 64, No. 5, May 1998, pp. 1878–1883.

* cited by examiner

*Primary Examiner*—Carla J. Myers
*Assistant Examiner*—Diana Johannsen
(74) *Attorney, Agent, or Firm*—Knobbe, Martens, Olson & Bear, LLP

(57) ABSTRACT

The invention relates to the nitrification of wastewater and identification of microorganisms capable of participating in this process. Specifically, the invention provides a consortium of microorganisms capable of nitrite oxidation in wastewater, which consortium is enriched in members of the Nitrospira phylum. The invention also provides oligonucleotide primers and probes for the amplification or detection of Nitrospira DNA, kits comprising the primers and probes, and methods of detection and quantitating Nitrospira species in a sample.

4 Claims, 17 Drawing Sheets

```
[    1                                                                      50 ]
SBR1024---------- ---------- ---------- ---------- ----------
SBR1015---------- ---------- ---------- ---------- ----------
  GC86  ---------- ----------   --UCGACCUG CAGGCGGCCG CACUAGUGAU
SBR2046---------- ---------- ---------- ---------- ----------
  RC25  --------GC UCUCCCAUAU GGUCGACCUG CAGGCGGCCG CACUAGUGAU
  RC19  ---------- ---------- ---------- ---------- ----------
SBR2016---------- ---------- ---------- ---------- ----------
   RC7  ---------- ---------- ---------- ---------- ----------
  RC14  ---------- ---------- ---------- ---------- ----------
  RC99  ---------- ---------- ---------- ---------- ----------
  RC11  ---------- ---------- ---------- ---------- ----------
  RC73  ---------- ---------- ---------- ---------- ----------
  RC90  ---------- ---------- ---------- ---------- ----------

[   51                                                                     100 ]
SBR1024---------- ---------- ---------- ---------- ----------
SBR1015---------- ---------- ---------- ---------- --UAAUACAU
  GC86  UAGAGUUUGA UCCUGGCUCA GAACGAACGC UGGCGGCGCG CCUAAUACAU
SBR2046---------- ---------- ---------- ---------- ----------
  RC25  UAGAGUUUGA UCCUGGCUCA GAACGAACGC UGGCGGCGCG CCUAAUACAU
  RC19  ---------- ---------- ---------- ---------- ----------
SBR2016---------- ---------- ---------- ---------- --UAAUACAU
   RC7  ---------- ---------- ---------- ---------- --UAAUACAU
  RC14  ---------- ---------- ---------- ---------- ----------
  RC99  ---------- ---------- ---------- ---------- CCUAAUACAU
  RC11  ---------- ---------- ---------- ---------- ---AAUACAU
  RC73  ---------- ---------- ---------- ---------- ---AAUACAU
  RC90  ---------- ---------- ---------- ---------- --UAAUACAU

[  101                                                                     150 ]
SBR1024-CAAGUCGAG CGAGAAGACG UA......... ...GCAA... ........UA
SBR1015GCAAGUCGAG CGAGAAGACG UA......... ...GCAA... ........UA
  GC86  GCAAGUCGAG CGAGAAGACG UA......... ...GCAA... ........UA
SBR2046---------- CGAGAAGACG UA......... ...GCAA... ........UA
  RC25  GCAAGUCGAG CGAGAAGACG UA......... ...GCAA... ........UA
  RC19  --AAGUCGAG CGAGAAGGUG UA......... ...GCAA... ........UA
SBR2016GCAAGUCGAG CGAGAAGGUG UA......... ...GCAA... ........UA
   RC7  GCAAGUCGAG CGAGAAGGUG UA......... ...GCAA... ........UA
  RC14  ---------- CGAGAAGGUG UA......... ...GCAA... ........UA
  RC99  GCAAGUCGAU CGAGAAGGUG UA......... ...GCAA... ........UA
  RC11  GCAAGUCGAU CGAGAAGGUG UA......... ...GCAA... ........UA
  RC73  GCAAGUCGAU CGANAAGGUG UA......... ...GCAA... ........UA
  RC90  GCAAGUCGAU CGANAAGGUG UA......... ...GCAA... ........UA
```

Fig. 8A

```
[  151                                                             200 ]
SBR1024CGUUUGUAAA GCGGC..... ..GAACGGGU GAGGAAUACA UGGGUAACCU
SBR1015CGUUUGUAAA GCGGC..... ..GAACGGGU GAGGAAUACA UGGGUAGCCU
  GC86 CGUUUGUAAA GCGGC..... ..GAACGGGU GAGGAAUACA UGGGUAACCU
SBR2046CGUUUGUAAA GCGGC..... ..GAACGGGU GAGGAAUACA UGGGUAACCU
  RC25 CGUUUGUAAA GCGGC..... ..GAACGGGU GAGGAAUACA UGGGUAAUCU
  RC19 CACUUGUAAA GCGGC..... ..GAACGGGU GAGGAAUACA UGGGUAAUCU
SBR2016CACUUGUAAA GCGGC..... ..GAACGGGU GAGGAAUACA UGGGUAAUCU
  RC7  CACUUGUAAA GCGGC..... ..GAACGGGU GAGGAAUACA UGGGUAAUCU
  RC14 CACUUGUAAA GCGGC..... ..GAACGGGU GAGGAAUACA UGGGUAAUCU
  RC99 CACUUGUAAA GCGGC..... ..GAACGGGU GAGGAAUACA UGGGUAAUCU
  RC11 CACUUGUAAA GCGGC..... ..GAACGGGU GAGGAAUACA UGGGUAAUCU
  RC73 CACUUGUAAA GCGGC..... ..GAACGGGU GAGGAAUACA UGGGUAAUCU
  RC90 CACUUGUAAA GCGGC..... ..GAACGGGU GAGGAAUACA UGGGUAAUCU

[  201                                                             250 ]
SBR1024ACCUUCGAGU GGGGAAUAAC UAGCCGAAAG GUUAGCUAAU ACCGCAUACG
SBR1015ACCCUCGAGU GGGGAAUAAC UAACCGAAAG GUUAGCUAAU ACCGCAUACG
  GC86 ACCCUCGAGU GGGGAAUAAC UAGCCGAAAG GUUAGCUAAU ACCGCAUACG
SBR2046ACCCUCGAGU GGGGAAUAAC UAACCGAAAG GUUAGCUAAU ACCGCAUACG
  RC25 ACCAUCGAGU GGGGAAUAAC CAACCGAAAG GUUGGCUAAU ACCGCGUACG
  RC19 ACCAUCGAGU GGGGAAUAAC CAGCCGAAAG GUUGGCUAAU ACCGCGUACG
SBR2016ACCAUCGAGU GGGGAAUAAC CAACCGAAAG GUUGGCUAAU ACCGCGUACG
  RC7  ACCAUCGAGU GGGGAAUAAC CAACCGAAAG GUUGGCUAAU ACCGCGUACG
  RC14 ACCAUCGAGU GGGGAAUAAC CAACCGAAAG GUUGGCUAAU ACCGCGUACG
  RC99 ACCAUCGAGU GGGGAAUAAC CAACCGAAAG GUUGGCUAAU ACCGCGUACG
  RC11 ACCAUCGAGU GGGGAAUAAC CAACCGAAAG GUUGGCUAAU ACCGCGUACG
  RC73 ACCAUCGAGU GGGGAAUAAC CAACCGAAAG GUUGGCUAAU ACCGCGUACG
  RC90 ACCAUCGAGU GGGGAAUAAC CAACCGAAAG GUUGGCUAAU ACCGCGUACG

[  251                                                             300 ]
SBR1024ACUCCUGGUC .UGC..GGAU CGGGAGAGAA AGCGAUACC. ......GUG.
SBR1015GCUCCUGGUC .UGC..GGAU CGGGAGAGAA AGCGAUACC. ......GUG.
  GC86 ACUCCUGGUC .UGC..GGAU CGGGAGAGAA AGCGAUACC. ......GUG.
SBR2046GCUCCUGGUC .UGC..GGAU CGGGAGAGAA AGCGAUACC. ......GUG.
  RC25 CUUCUGAGUC .UUC..GGGU UCGGAAGGAA AGCCGUACU. ......GUG.
  RC19 CUUCCGAGUC .UUC..GGGC UUGGAAGGAA AGCCGCACU. ......GUG.
SBR2016CUUCUGAGCC .UUC..GUGU UCGGAAGGAA AGCCGUACU. ......GUG.
  RC7  CCUCCGAGUC .UUC..GGGU UCGGAGGGAA AGCUGCACU. ......GUG.
  RC14 CCUCCGAGUC .UUC..GGGU UCGGAGGGAA AGCUGCACU. ......GUG.
  RC99 CCUCCGAGUC .UUC..GGGU UCGGAGGGAA AGCUGCACU. ......GUG.
  RC11 CCUCCGAGUC .UUC..GGGU UCGGAGGGAA AGCUGCACU. ......GUG.
  RC73 CCUCCGAGUC .UUC..GGGU UCGGAGGGAA AGCUGCACU. ......GUG.
  RC90 CUUCCGAGUC .UUC..GGGC UUGGAAGGAA AGCCGCACU. ......GUG.
```

Fig. 8B

```
[    301                                                             350  ]
SBR1024.....GGUAU CGCGCUCUUG GAUGGGCUCA UGUCCUAUCA GCUUGUUGGU
SBR1015.....GGUAU CGCGCUCUUG GAUGGGCUCA UGUCCUAUCA GCUUGUUGGU
  GC86  .....GGUAU CGCGCUCUUG GAUGGGCUCA UGUCCUAUCA GCUUGUUGGU
SBR2046.....GGUAU CGCGCUCUUG GAUGGGCUCA UGUCCUAUCA GCUUGUUGGU
  RC25  .....AGUGC GGCGCUCUUU GAUGAGCUCA UGUCCUAUCA GCUUGUUGGU
  RC19  .....AGUGC GGCGCUCUUU GAUGAGCUCA UGUCCUAUCA GCUUGUUGGU
SBR2016.....AGUGC GGCGCUCUUU GAUGAGCUCA UGUCCUAUCA GCUUGUUGGU
   RC7  .....AGUGU AGCGCUCUUU GAUGAGCUCA UGUCCUAUCA GCUUGUUGGU
  RC14  .....AGUGU AGCGCUCUUU GAUGAGCUCA UGUCCUAUCA GCUUGUUGGU
  RC99  .....AGUGU AGCGCUCUUU GAUGAGCUCA UGUCCUAUCA GCUUGUUGGU
  RC11  .....AGUGU AGCGCUCUUU GAUGAGCUCA UGUCCUAUCA GCUUGUUGGU
  RC73  .....AGUGU AGCGCUCUUU GAUGAGCUCA UGUCCUAUCA GCUUGUUGGU
  RC90  .....AGUGC GGCGCUCUUU GAUGAGCUCA UAUCCUAUCA NCUUGUUGGU

[    351                                                             400  ]
SBR1024GAGGUAACGG CUCACCAAGG CUUCGACGGG UAGCUGGUCU GAGAGGACGA
SBR1015GAGGUAACGG CUCACCAAGG CUUCGACGGG UAGCUGGUCU GAGAGGACGA
  GC86  GAGGUAACGG CUCACCAAGG CUUCGACGGG UAGCUGGUCU GAGAGGACGA
SBR2046GAGGUAACGG CUCACCAAGG CUUCGACGGG UAGCUGGUCU GAGAGGACGA
  RC25  AGGGUAACGG CCUACCAAGG CUUUGACGGG UAGCUGGUCU GAGAGGACGA
  RC19  AGGGUAACGG CCUACCAAGG CUUUGACGGG UAGCUGGUCU GAGAGGACGA
SBR2016AGGGUAACGG CCUACCAAGG CUUUGACGGG UAGCUGGUCU GAGAGGACGA
   RC7  AGGGUAACGG CCUACCAAGG CUUUGACGGG UAGCUGGUCU GAGAGGACGA
  RC14  AGGGUAACGG CCUACCAAGG CUUUGACGGG UAGCUGGUCU GAGAGGACGA
  RC99  AGGGUAACGG CCUACCAAGG CUUUGACGGG UAGCUGGUCU GAGAGGACGA
  RC11  AGGGUAACGG CCUACCAAGG CUUUGACGGG UAGCUGGUCU GAGAGGACGA
  RC73  AGGGUAACGG CCUACCAAGG CUUUGACGGG UAUCUGGUCU GAGAGGACGA
  RC90  AGGGUAACGG CCUACCAAGG CUUUGACGGG UAUCUGGUCU GAGAGGACGA

[    401                                                             450  ]
SBR1024UCAGCCACAC UGGCACUGCG ACACGGGCCA GACUCCUACG GGAGGCAGCA
SBR1015UCAGCCACAC UGGCACUGCG ACACGGGCCA GACUCCUACG GGAGGCAGCA
  GC86  UCAGCCACAC UGGCACUGCG ACACGGGCCA GACUCCUACG GGAGGCAGCA
SBR2046UCAGCCACAC UGGCACUGCG ACACGGGCCA GACUCCUACG GGAGGCAGCA
  RC25  UCAGCCACAC UGGCACUGCG ACACGGGCCA GACUCCUACG GGAGGCAGCA
  RC19  UCAGCCACAC UGGCACUGCG ACACGGGCCA GACUCCUACG GGAGGCAGCA
SBR2016UCAGCCACAC UGGCACUGCG ACACGGGCCA GACUCCUACG GGAGGCAGCA
   RC7  UCAGCCACAC UGGCACUGCG ACACGGGCCA GACUCCUACG GGAGGCAGCA
  RC14  UCAGCCACAC UGGCACUGCG ACACGGGCCA GACUCCUACG GGAGGCAGCA
  RC99  UCAGCCACAC UGGCACUGCG ACACGGGCCA GACUCCUACG GGAGGCAGCA
  RC11  UCAGCCACAC UGGCACUGCG ACACGGGCCA GACUCCUACG GGAGGCAGCA
  RC73  UCAGCCACAC UGGCACUGCG ACACGGGCCA GACUCCUACG GGAGGCAGCA
  RC90  UCAGCCACAC UGGCACUGCG ACACGGGCCA GACUCCUACG GGAGGCAGCA
```

Fig. 8C

[    451                                                            500  ]
SBR1024 GUAAGGAAUA UUGCGCAAUG GGC.GACAGC CUGACGCAGC NACGCCGCGU
SBR1015 GUAAGGAAUA UUGCGCAAUG GGC.GACAGC CUGACGCAGC NACGCCGCGU
 GC86   GUAAGGAAUA UUGCGCAAUG GGC.GACAGC CUGACGCAGC NACGCCGCGU
SBR2046 GUAAGGAAUA UUGCGCAAUG GGC.GACAGC CUGACGCAGC GACGCCGCGU
 RC25   GUAAGGAAUA UUGCGCAAUG GGC.GAAAGC CUGACGCAGC NACGCCGCGU
 RC19   GUAAGGAAUA UUGCGCAAUG GGC.GAAAGC CUGACGCAGC GACGCCGCGU
SBR2016 GUAAGGAAUA UUGCGCAAUG GGC.GAAAGC CUGACGCAGC NACGCCGCGU
 RC7    GUAAGGAAUA UUGCGCAAUG GGC.GAAAGC CUGACGCAGC NACGCCGCGU
 RC14   GUAAGGAAUA UUGCGCAAUG GGC.GAAAGC CUGACGCAGC NACGCCGCGU
 RC99   GUAAGGAAUA UUGCGCAAUG GGC.GAAAGC CUGACGCAGC CACGCCGCGU
 RC11   GUAAGGAAUA UUGCGCAAUG GGC.GAAAGC CUGACGCAGC CACGCCGCGU
 RC73   GUAAGGAAUA UUGCGCAAUG GGC.GAAACC CNGACGCAGC CACGCCGCGU
 RC90   GUAAGGAAUA UUGCGCAAUG GGC.GAAACC CNGACGCAGC CACGCCGCGU

[    501                                                            550  ]
SBR1024 GGGGGAUGAA GGUC.UUCGG AUUGUAAACC CCUUUCGGCA GGGAAGAUGG
SBR1015 GGGGGAUGAA GGUC.UUCGG AUUGUAAACC CCUUUCGGCA GGGAAGAUGG
 GC86   GGGGGAUGAA GGUC.UUCGG AUUGUAAACC CCUUUCGGCA GGGAAGAUGG
SBR2046 UGGGGAUGAA AGUC.UUCCG AUUGUAAACC CCUUUCCGCA GGGAAGAUGG
 RC25   GGGGGAUGAA GGUC.UUCGG AUUGUAAACC CCUUUCGGGA GGGAAGAUGG
 RC19   GGGGGAUGAA GGUC.UUCGG AUUGUAAACC CCUUUCGGGA GGGAAGAUGG
SBR2016 GGGGGAUGAA GGUC.UUCGG AUUGUAAACC CCUUUCGGGA GGGAAGAUGG
 RC7    GGGGGAUGAA GGUC.UUCGG AUUGUAAACC CCUUUCGGGA GGGAAGAUGG
 RC14   GGGGGAUGAA GGUC.UUCGG AUUGUAAACC CCUUUCGGGA GGGAAGAUGG
 RC99   GGGGGAUGAA GGUC.UUCGG AUUGUAAACC CCUUUCGGGA GGGAAGAUGG
 RC11   GGGGGAUGAA GGUC.UUCGG AUUGUAAACC CCUUUCGGGA GGGAAGAUGG
 RC73   GGGGGAUGAA GGUC.UUCGG AUUGUAAACC CCUUUCGGGA GGGAAGAUGG
 RC90   GGGGGAUGAA GGUC.UUCGG AUUGUAAACC CCUUUCGGGA GGGAAGAUGG

[    551                                                            600  ]
SBR1024 AACGG..... .GUAA..... ...CCGUUCG GACGGUACCU GCAGAAGCAG
SBR1015 AACGG..... .GUAA..... ...CCGUUCG GACGGUACCU GCAGAAGCAG
 GC86   AACGG..... .GUAA..... ...CCGUUCG GACGGUACCU GCAGAAGCAG
SBR2046 AACGG..... .GUAA..... ...CCGUUCG GACGGUACCU GCAGAAGCAG
 RC25   AGCGA..... .GCAA..... ...UCGUUCG GACGGUACCU CCAGAAGCAG
 RC19   AGCCA..... .GCAA..... ...UCGUUCG GACGGUACCU CCAGAAGCAG
SBR2016 AGCGA..... .GCAA..... ...UCGUUCG GACGGUACCU CCAGAAGCAG
 RC7    AGCGA..... .GCAA..... ...UCGUUCG GACGGUACCU CCAGAAGCAG
 RC14   AGCGA..... .GCAA..... ...UCGUUCG GACGGUACCU CCAGAAGCAG
 RC99   AGCGA..... .GCAA..... ...UCGUUCG GACGGUACCU CCAGAAGCAG
 RC11   AGCGA..... .GCAA..... ...UCGUUCG GACGGUACCU CCAGAAGCAG
 RC73   AACGA..... .GCAA..... ...UCGUUCG GACGGUACCU CCAGAAGCAG
 RC90   AACGA..... .GCAA..... ...UCGUUCG GACGGUACCU CCAGAAGCAG

*Fig. 8D*

```
[   601                                                                     650 ]
SBR1024 CCACGGCUAA CUUCGUGCCA GCAGCCGCGG UAAUACGAAG GUGGCAAGCG
SBR1015 CCACGGCUAA CUUCGUGCCA GCAGCCGCGG UAAUACGAAG GUGGCAAGCG
  GC86  CCACGGCUAA CUUCGUGCCA GCAGCCGCGG UAAUACGAAG GUGGCAAGCG
SBR2046 CCACGGCUAA CUUCGUGCCA GCAGCCGCGG UAAUACGAAG GUGGCAAGCG
  RC25  CCACGGCCAA CUUCGUGCCA GCAGCCGCGG UAAUACGAAG GUGGCAAGCG
  RC19  CCACGGCCAA CUUCGUGCCA GCAGCCGCGG UAAUACGAAG GUGGCAAGCG
SBR2016 CCACGGCCAA CUUCGUGCCA GCAGCCGCGG UAAUACGAAG GUGGCAAGCG
   RC7  CCACGGCCAA CUUCGUGCCA GCAGCCGCGG UAAUACGAAG GUGGCAAGCG
  RC14  CCACGGCCAA CUUCGUGCCA GCAGCCGCGG UAAUACGAAG GUGGCAAGCG
  RC99  CCACGGCCAA CUUCGUGCCA GCAGCCGCGG UAAUACGAAG GUGGCAAGCG
  RC11  CCACGGCCAA CUUCGUGCCA GCAGCCGCGG UAAUACGAAG GUGGCAAGCG
  RC73  CCACGGCCAA CUUCGUGCCA GCAGCCGCGG UAAUACGAAG GUGGCAAGCG
  RC90  CCACGGCCAA CUUCGUGCCA GCAGCCGCGG UAAUACGAAG GUGGCAAGCG

[   651                                                                     700 ]
SBR1024 UUGUUCGGAU UUACUGGGCG UACAGGGAGC GUAGGCGGUU GGGUAAGCCC
SBR1015 UUGUUCGGAU UUACUGGGCG UACAGGGAGC GUAGGCGGUU GGGUAAGCCC
  GC86  UUGUUCGGAU UUACUGGGCG UACAGGGAGC GUAGGCGGUU GGGUAAGCCC
SBR2046 UUGUUCGGAU UUACUGGGCG UACAGGGAGC GUAGGCGGUU GGGUAAGCCC
  RC25  UUGUUCGGAU UCACUGGGCG UACAGGGUGU GUAGGCGGUU UGGUAAGCCU
  RC19  UUGUUCGGAU UCACUGGGCG UACAGGGUGU GUANGCGGUU UGGUAAGCCU
SBR2016 UUGCUUGGAU UCACUGGGCG UACAGGGUGU GUAGGCGGUU UGGUAAGCCU
   RC7  UUGUUCGGAU UCACUGGGCG UACAGGGUGU GUAGGCGGUU UGGUAAGCCU
  RC14  UUGUUCGGAU UCACUGGGCG UACAGGGUGU GUAGGCGGUU UGGUAAGCCU
  RC99  UUGUUCGGAU UCACUGGGCG UACAGGGUGU GUAGGCGGUU UGGUAAGCCU
  RC11  UUGUUCGGAU UCACUGGGCG UACAGGGUGU GUAGGCGGUU UGGUAAGCCU
  RC73  UUGUUCGGAU UCACUGGGCG UACAGGGUGU GUAGGCGGUU UGGUAAGCCU
  RC90  UUGUUCGGAU UCACUGGGCG UACAGGGUGU GUAGGCGGUU UGGUAAGCCU

[   701                                                                     750 ]
SBR1024 UCCGUGAAAU CUCCGGGCCU AACCCGGAAA GUGCGGAGGG GACUGCUCGG
SBR1015 UCCGUGAAAU CUCCGGGCCU AACCCGGAAA GUGCGGAGGG GACUGCUCGG
  GC86  UCCGUGAAAU CUCCGGGCCU AACCCGGAAA GUGCGGAGGG GACUGCUCGG
SBR2046 UCCGUGAAAU CUCCGGGCCU AACCCGGAAA GUGCGGAGGG GACUGCUCGG
  RC25  UCUGUUAAAG CUUCGGGCCC AACCCGGAAA GCGCAGACGG UACUGCCAGG
  RC19  UCUGUUAAAG CUUCGGGCCC AACCCGGAAA GCGCAGAGGG UACUGCCAGG
SBR2016 UCUGUUAAAG CUUCGGGCCC AACCCGAAAA GCGCAGAGGG UACUGCCAGG
   RC7  UCUGUUAAAG CUUCGGGCCC AACCCGGAAA GCGCAGGGGG UACUGCCAGG
  RC14  UCUGUUAAAG CUUCGGGCCC AACCCGGAAA GCGCAGAGGG UACUGCCAGG
  RC99  UCUGUUAAAG CUUCGGGCCC AACCCGGAAA GCGCAGAGGG UACUGCCAGG
  RC11  UCUGUUAAAG CUUCGGGCCC AACCCGGAAA GCGCAGAGGG UACUGCCAGG
  RC73  UCUGUUAAAG CUUCGGGCCC AACCCGGAAA GCGCAGAGGG UACUGCCAGG
  RC90  UCUGUUAAAG CUUCGGGCCC AACCCGGAAA GCGCAGAGGG UACUGCCAGG
```

*Fig. 8E*

```
[    751                                                          800  ]
SBR1024CUAGAGGAUG GGAGAGGAGC GCGGAAUUCC CGGUGUAGCG GUGAAAUGCG
SBR1015CUAGAGGAUG GGAGAGGAGC GCGGAAUUCC CGGUGUAGCG GUGAAAUGCG
  GC86 CUAGAGGAUG GGAGAGGAGC GCGGAAUUCC CGGUGUAGCG GUGAAAUGCG
SBR2046CUAGAGGAUG GGAGAGGAGC GCGGAAUUCC CGGUGUAGCG GUGAAAUGCG
  RC25 CUAGAGGGUG GGAGAGGAGC GCGGAAUUCC CGGUGUAGCG GUGAAAUGCG
  RC19 CUAGAGGGUG GGAGAGGAGC GCGGAAUUCC CGGUGUAGCG GUGAAAUGCG
SBR2016CUAGAGGGUG GGAGAGGAGC GCGGAAUUCC CGGUGUAGCG GUGAAAUGCG
   RC7 CUAGAGGGUG GGAGAGGAGC GCGGAAUUCC CGGUGUAGCG GUGAAAUGCG
  RC14 CUAGAGGGUG GGAGAGGAGC GCGGAAUUCC CGGUGUAGCG GUGAAAUGCG
  RC99 CUAGAGGGUG GGAGAGGAGC GCGGAAUUCC CGGUGUAGCG GUGAAAUGCG
  RC11 CUAGAGGGUG GGAGAGGAGC GCGGAAUUCC CGGUGUAGCG GUGAAAUGCG
  RC73 CUAGAGGGUG GGAGAGGAGC GCGGAAUUCC CGGUGUAGCG GUGAAAUGCG
  RC90 CUAGAGGGUG GGAGAGGAGC GCGGAAUUCC CGGUGUAGCG GUGAAAUGCG

[    801                                                          850  ]
SBR1024UAGAGAUCGG GAGGAAGGCC GGUGGCGAAG GCGGCGCUCU GGAACAUUUC
SBR1015UAGAGAUCGG GAGGAAGGCC GGUGGCGAAG GCGGCGCUCU GGAACAUUUC
  GC86 UAGAGAUCGG GAGGAAGGCC GGUGGCGAAG GCGGCGCUCU GGAACAUUUC
SBR2046UAGAGAUCGG GAGGAAGGCC GGUGGCGAAG GCGGCGCUCU GGAACAUUUC
  RC25 UAGAGAUCGG GAGGAAGGCC GGUGGCGAAG GCGGCGCUCU GGAACAUACC
  RC19 UAGAGAUCGG GAGGAAGGCC GGUGGCGAAG GCGGCGCUCU GGAACAUGCC
SBR2016UAGAGAUCGG GAGGAAGGCC GGUGGCGAAG GCGGCGCUCU GGAACAUACC
   RC7 UAGAGAUCGG GAGGAAGGCC GGUGGCGAAG GCGGCGCUCU GGAACAUACC
  RC14 UAGAGAUCGG GAGGAAGGCC GGUGGCGAAG GCGGCGCUCU GGAACAUACC
  RC99 UAGAGAUCGG GAGGAAGGCC GGUGGCGAAG GCGGCGCUCU GGAACAUACC
  RC11 UAGAGAUCGG GAGGAAGGCC GGUGGCGAAG GCGGCGCUCU GGAACAUACC
  RC73 UAGAGAUCGG GAGGAAGGCC GGUGGCGAAG GCGGCGCUCU GGAACAUACC
  RC90 UAGAGAUCGG GAGGAAGGCC GGUGGCGAAG GCGGCGCUCU GGAACAUACC

[    851                                                          900  ]
SBR1024UGACGCUGAG GCUCGAAAGC GUGGGGAGCA AACAGGAUUA GAUACCCUGG
SBR1015UGACGCUGAG GCUCGAAAGC GUGGGGAGCA AACAGGAUUA GAUACCCUGG
  GC86 UGACGCUGAG GCUCGAAAGC GUGGGGAGCA AACAGGAUUA GAUACCCUGG
SBR2046UGACGCUGAG GCUCGAAAGC GUGGGGAGCA AACAGGAUUA GAUACCCUGG
  RC25 UGACGCUGAG ACACGAAAGC GUGGGGAGCA AACAGGAUUA GAUACCCUGG
  RC19 UGACGCUGAG ACACGAAAGC GUGGGGAGCA AACAGGAUUA GAUACCCUGG
SBR2016UGACGCUGAG ACACGAAAAC GUGGGGAGCA AACAGGAUUA GAUACCCUGG
   RC7 UGACGCUGAG ACACGAAAGC GUGGGGAGCA AACAGGAUUA GAUACCCUGG
  RC14 UGACGCUGAG ACACGAAAGC GUGGGGAGCA AACAGGAUUA GAUACCCUGG
  RC99 UGACGCUGAG ACACGAAAGC GUGGGGAGCA AACAGGAUUA GAUACCCUGG
  RC11 UGACGCUGAG ACACGAAAGC GUGGGGAGCA AACAGGAUUA GAUACCCUGG
  RC73 UGACGCUGAG ACACGAAAGC GUGGGGNGCA AACAGGAUUA GAUACCCUGG
  RC90 UGACGCUCAG ACACGAAAGC GUGGGGAGCA AACAGGAUUA GAUACCCUGG
```

*Fig. 8F*

```
[    901                                                                   950  ]
SBR1024 UAGUCCACGC CUUAAACGAU GGAUACUAAG UGUCGGCGG. ..........
SBR1015 UAGUCCACGC CUUAAACGAU GGAUACUAAG UGUCGGCGG. ..........
   GC86 UAGUCCACGC CUUAAACGAU GGAUACUAAG UGUCGGCGG. ..........
SBR2046 UAGUCCACGC CUUAAACGAU GGAUACUAAG UGUCGGCGG. ..........
   RC25 UAGUCCACGC CCUAAACUAU GGAUACUAAG UGUCGGCGG. ..........
   RC19 UAGUCCACGC CCUAAACUAU GGAUACUAAG UGUCGGCGG. ..........
SBR2016 UAGUCCACGC CCUAAACUAU GGAUACUAAG UGUCGGCGG. ..........
    RC7 UAGUCCACGC CCUAAGCUAU GGAUACUAAG UGUCGGCGG. ..........
   RC14 UAGUCCACGC CCUAAACUAU GGAUACUAAG UGUCGGCGG. ..........
   RC99 UAGUCCACGC CCUAAACUAU GGAUACUAAG UGUCGGCGG. ..........
   RC11 UAGUCCACGC CCUAAACUAU GGAUACUAAG UGUCGGCGG. ..........
   RC73 UAGUCCACGC CCUAAACUAU GGAUACUAAG UGUCGGCGG. ..........
   RC90 UAGUCCACGC CCUAAACUAU GGAUACUAAG UGUCGGCGG. ..........

[    951                                                                  1000  ]
SBR1024 .........G UUA....... .......... .CCGCCGGUG CCGCAGCUAA
SBR1015 .........G UUA....... .......... .CCGCCGGUG CCGCAGCUAA
   GC86 .........G UUA....... .......... .CCGCCGGUG CCGCAGCUAA
SBR2046 .........G UUA....... .......... .CCGCCGGUG CCGCAGCUAA
   RC25 .........G UUA....... .......... .CCGCCGGUG CCGCAGCUAA
   RC19 .........G UUA....... .......... .CCGCCGGUG CCGCAGCUAA
SBR2016 .........G UUA....... .......... .CCGCCGGUG CCGCAGCUAA
    RC7 .........G UUA....... .......... .CCGCCGGUG CCGCAGCCAA
   RC14 .........G UUA....... .......... .CCGCCGGUG CCGCAGCUAA
   RC99 .........G UUA....... .......... .CCGCCGGUG CCGCAGCUAA
   RC11 .........G UUA....... .......... .CCGCCGGUG CCGCAGCUAA
   RC73 .........G UUA....... .......... .CCGCCGGUG CCGCAGCUAA
   RC90 .........G UUA....... .......... .CCGCCGGUG CCGCAGCUAA

[   1001                                                                  1050  ]
SBR1024 CGCAUUAAGU AUCCCGCCUG GGAAGUACGG CCGCAAGGUU GAAACUCAAA
SBR1015 CGCAUUAAGU AUCCCGCCUG GGAAGUACGG CCGCAAGGUU GAAACUCAAA
   GC86 CGCAUUAAGU AUCCCGCCUG GGAAGUACGG CCGCAAGGUU GAAACUCAAA
SBR2046 CGCAUUAAGU AUCCCGCCUG GGAAGUACGG CCGCAAGGUU GAAACUCAAA
   RC25 CGCAUUAAGU AUCCCGCCUG GGAAGUACGG CCGCAAGGUU GAAACUCAAA
   RC19 CGCAUUAAGU AUCCCGCCUG GGAAGUACGG CCGCAAGGUU GAAACUCAAA
SBR2016 CGCAUUAAGU AUCCCGCCUG GGAGGUACGG CCGCAAGGUU GAAACUCAAA
    RC7 CGCGUUAAGU AUCCCGCCUG GGAAGUACGG CCGCAAGGUU GAAACUCAAA
   RC14 CGCAUUAAGU AUCCCGCCUG GGAAGUACGG CCGCAAGGUU GAAACUCAAA
   RC99 CGCAUUAAGU AUCCCGCCUG GGAAGUACGG CCGCAAGGUU GAAACUCAAA
   RC11 CGCAUUAAGU AUCCCGCCUG GGAAGUACGG CCGCAAGGUU GAAACUCAAA
   RC73 CGCAUUAAGU AUCCCGCCUG GGAAGUACGG CCGCAAGGUU GAAACUCAAA
   RC90 CGCAUUAAGU AUCCCGCCUG GGAAGUACGG CCGCAAGGUU GAAACUCAAA
```

*Fig. 8G*

```
[ 1051                                                              1100 ]
SBR1024 GGAAUUGACG  GGGGCCCGCA  CAAGCGGUGG  AGCAUGUGGU  UUAAUUCGAC
SBR1015 GGAAUUGACG  GGGGCCCGCA  CAAGCGGUGG  AGCAUGUGGU  UUAAUUCGAC
  GC86  GGAAUUGACG  GGGGCCCGCA  CAAGCGGUGG  AGCAUGUGGU  UUAAUUCGAC
SBR2046 GGAAUUGACG  GGGCCCGCA   CAAGCGGUGG  AGCAUGUGGU  UUAAUUCGAC
  RC25  GGAAUUGACG  GGGGCCCGCA  CAAGCGGUGG  AGCAUGUGGU  UUAAUUCGAC
  RC19  GGAAUUGACG  GGGGCCCGCA  CAAGCGGUGG  AGCAUGUGGU  UUAAUUCGAC
SBR2016 GGAAUUGACG  GGGGCCCGCA  CAAGCGGUGG  AGCUUGUGGU  UUAAUUCGAC
  RC7   GGAAUUGACG  GGGGCCCGCA  CAAGCGGUGG  AGCAUGUGGU  UUAAUUCGAC
  RC14  GGAAUUGACG  GGGGCCCGCA  CAAGCGGUGG  AGCAUGUGGU  UUAAUUCGAC
  RC99  GGAAUUGACG  GGGGCCCGCA  CAAGCGGUGG  AGCAUGUGGU  UUAAUUCGAC
  RC11  GGAAUUGACG  GGGGCCCGCA  CAAGCGGUGG  AGCAUGUGGU  UUAAUUCGAC
  RC73  GGGAUUGACG  GGGGCCCGCA  CAAGCGGUGG  GGCAUGUGGU  UUAAUUCGAC
  RC90  GGAAUUGACG  GGGGCCCGCA  CAAGCGGUGG  AGCAUGUGGU  UUAAUUCGAC

[ 1101                                                              1150 ]
SBR1024 GCAACGCGAA  GAACCUUA.C  CCAGGCUGGA  CAUG......  ...CAGGUAG
SBR1015 GCAACGCGAA  GAACCUUA.C  CCAGGCUGGA  CAUG......  ...CAGGUAG
  GC86  GCAACGCGAA  GAACCUUA.C  CCAGGCUGGA  CAUG......  ...CAGGUAG
SBR2046 GCAACGCGAA  GAACCUUA.C  CCAGGCAGGA  CAUG......  ...CAGGUAG
  RC25  GCAACGCGAA  GAACCUUA.C  CCAGGUUGGA  CAUG......  ...CACGUAG
  RC19  GCAACGCGAA  GAACCUUA.C  CCAGGUUGGA  CAUG......  ...CACGUAG
SBR2016 GCAACGCGAA  GAACCUUA.C  CCAGGUUGGA  CAUG......  ...CACGUAG
  RC7   GCAACGCGAA  GAACCUUA.C  CCAGGUUGGA  CAUG......  ...CACGUAG
  RC14  GCAACGCGAA  GAACCUUA.C  CCAGGUUGGA  CAUG......  ...CACGUAG
  RC99  GCAACGCGAA  GAACCUUA.C  CCAGGUUGGA  CAUG......  ...CACGUAG
  RC11  GCAACGCGAA  GAACCUUA.C  CCAGGUUGGA  CAUG......  ...CACGUAG
  RC73  GCAACGCGAA  GAACCUUA.C  CCAGGUUGGA  CAUG......  ...CACGUAG
  RC90  GCAACGCGAA  GAACCUUA.C  CCAGGUUGGA  CAUG......  ...CACGUAG

[ 1151                                                              1200 ]
SBR1024 UAGAAGGGU.  .GAAA..GCC  UAACGAGGUA  .....GCAA.  ....UACCAU
SBR1015 UAGAAGGGU.  .GAAA..GCC  UAACGAGGUA  .....GCAA.  ....UACCAU
  GC86  UAGAAGGGU.  .GAAA..GCC  UAACGAGGUA  .....GCAA.  ....CACCAU
SBR2046 UAGAAGGGU.  .GAAA..GCC  UAACGAGGUA  .....GCAA.  ....UACCAU
  RC25  UAGAAAGGU.  .GAAA..GCC  UGACGAGGUA  .....GCAA.  ....UACCAG
  RC19  UAGAAAGGU.  .GAAA..GNC  UAACGAGGUA  .....GCAA.  ....UACCAG
SBR2016 UAGAAAGGU.  .GAAA..GCC  UGACGAGGUA  .....GCAA.  ....UACCAG
  RC7   UAGAAAGGU.  .GAAA..GCC  UGACGAGGUA  .....GCAA.  ....UACCAG
  RC14  UAGAAAGGU.  .GAAA..GCC  UGACGAGGUA  .....GCAA.  ....UACCAG
  RC99  UAGAAAGGU.  .GAAA..GCC  UGACGAGGUA  .....GCAA.  ....UACCAG
  RC11  UANAAAGGU.  .GAAA..GCC  UGACGAGGUA  .....GCAA.  ....UACCAG
  RC73  UNGAAAGGU.  .GAAA..GCC  UGACGAGGUA  .....GCAA.  ....UACCAG
  RC90  UAGAAAGGU.  .GAAA..GCC  UGACGAGGUA  .....GCAA.  ....UACCAG
```

Fig. 8H

```
[ 1201                                                                 1250 ]
SBR1024 CCUGCUCAGG UGCUGCAUGG CUGUCGUCAG CUCGUGCCGU GAGGUGUUGG
SBR1015 CCUGCUCAGG UGCUGCAUGG CUGUCGUCAG CUCGUGCCGU GAGGUGUUGG
  GC86  CCUGCUCAGG UGCUGCAUGG CUGUCGUCAG CUCGUGCCGU GAGGUGUUGG
SBR2046 CCUGCUCAGG UGCUGCAUGG CUGUCGUCAG CUCGUGCCGU GAGGUGUUGG
  RC25   CGUGCUCAGG UGCUGCAUGG CUGUCGUCAG CUCGUGCCGU GAGGUGUUGG
  RC19   CGUGCUCAGG UGCUGCAUGG CUGUCGUCAG CUCGUGCCGU GAGGUGUUGG
SBR2016 CGUGCUCAGG UGCUGCAUGG CUGUCGUCAG CUCGUGCCGU GAGGUGUUGG
  RC7    CGUGCUCAGG UGCUGCAUGG CUGUCGUCAG CUCGUGCCGU GAGGUGUUGG
  RC14   CGUGCUCAGG UGCUGCAUGG CUGUCGUCAG CUCGUGCCGU GAGGUGUUGG
  RC99   CGUGCUCAGG UGCUGCAUGG CUGUCGUCAG CUCGUGCCGU GAGGUGUUGG
  RC11   CGUGCUCAGG UGCUGCAUGG CUGUCUUCAG CUCGUGCCGU GAGGUGUUGG
  RC73   CGUGCUCAGG UGCUGCAUGG CUGUCGUCAG CUCGUGCCGU GAGGUGUUGG
  RC90   CGUGCUCAGG UGCUGCAUGG CUGUCGUCAG CUCGUGCCGU GAGGUGUUGG

[ 1251                                                                 1300 ]
SBR1024 GUUAAGUCCC GCAACGAGCG CAACCCCUGU CUUCAGUUAC CAACGG....
SBR1015 GUUAAGUCCC GCAACGAGCG CAACCCCUGU CUUCAGUUAC CAACGG....
  GC86  GUUAAGUCCC GCAACGAGCG CAACCCCUGU CUUCAGUUAC CAACGG....
SBR2046 GUUAAGUCCC GCAACGAGCG CAACCCCUGU CUUCAGUUAC CAACGG....
  RC25   GUUAAGUCCC GCAACGAGCG CAACCCCUGC UUUCAGUUGC UACCGG....
  RC19   GUUAAGUCCC GCAACGAGCG CAACCCCUGC UUUCAGUUGC UACCGG....
SBR2016 GUUAAGUCCC GCAACGAGCG CAACCCCUGC UUUCAGUUGC UACCGG....
  RC7    GUUAAGUCCC GCAACGAGCG CAACCCCUGC UUUCAGUUGC UACCGG....
  RC14   GUUAAGUCCC GCAACGAGCG CAACCCCUGC UUUCAGUUGC UACCGG....
  RC99   GUUAAGUCCC GCAACGAGCG CAACCCCUGC UUUCAGUUGC UACCGG....
  RC11   GUUAAGUCCC GCAACGAGCG CAACCCCUGC UUUCAGUUGC UACCGG....
  RC73   GUUAAGUCCC GCAACGAGCG CAACCCCUGC UUUCAGUUGC UACCGG....
  RC90   GUUAAGUCCC GCAACGAGCG CAACCCCUGC UUUCAGUUGC UGCCGG....

[ 1301                                                                 1350 ]
SBR1024 GUCAUG.... CCGGGAACUC UGGAGAGACU GCCCAGGAGA ACGGG.GAGG
SBR1015 GUCAUG.... CCGGGAACUC UGGAGAGACU GCCCAGGAGA ACGGGGGAGG
  GC86  GUCAUG.... CCGGGAACUC UGGAGAGACU GCCCAGGAGA ACGGG.GAGG
SBR2046 GUCAUG.... CCGGGAACUC UGGAGAGACU GCCCAGGAGA ACGGG.GAGG
  RC25   GUCAUG.... CCGAGCACUC UGAAAGGACU GCCCAGGAUA ACGGG.GAGG
  RC19   GUCAUG.... CCGAGCACUC UGAAAGGACU GCCCAGGAUA ACGGG.GAGG
SBR2016 GUCAUG.... CCGAGCACUC UGAAAGGACU GCCCAGGAUA ACGGG.GAGG
  RC7    GUCAUG.... CCGAGCACUC UGAAAGGACU GCCCAGGAUA ACGGGGGAGG
  RC14   GUCAUG.... CCGAGCACUC UGAAAGGACU GCCCAGGAUA ACGGG.GAGG
  RC99   GUCAUG.... CCGAGCACUC UGAAAGGACU GCCCAGGAUA ACGGGGAAGG
  RC11   GUCAUG.... CCGAACACUC UGAAAGGACU GCCCAGGAUA ACGGGGAAGG
  RC73   GUCAUG.... CCGAACACUC UGAAAGGACU GCCCAGGAUA ACGGGGAAGG
  RC90   GUCAUG.... CCGAACACUC UGAAAGGACU GCCCAGGAUA ACGGGGAAGG
```

*Fig. 8I*

```
[  1351                                                              1400  ]
SBR1024AAGGUGGGGA UGACGUCAAG UCAGCAUGGC CUUUAUGCCU GGGGCCACAC
SBR1015AAGGUGGGGA UGACGUCAAG UCAGCAUGGC CUUUAUGCCU GGGGCCACAC
  GC86  AAGGUGGGGA UGACGUCAAG UCAGCAUGGC CUUUAUGCCU GGGGCCACAC
SBR2046AAGGUGGGGA UGACGUCAAG UCAGCAUGGC CUUUAUGCCU GGGGCCACAC
  RC25  AAGGUGGGGA UGACGUCAAG UCAGCAUGGC CUUUAUGCCU GGGGCCACAC
  RC19  AAGGUGGGGA UGACGUCAAG UCAGCAUGGC CUUUAUGCCU GGGGCCACAC
SBR2016AAGGUGGGGA UGACGUCAAG UCAGCAUGGC CUUUAUGCCU GGGGCCACAC
  RC7   AAGGUGGGGA UGACGUCAAG UCAGCAUGGC CUUUAUGCCU GGGGCCACAC
  RC14  AAGGUGGGGA UGACGUCAAG UCAGCAUGGC CUUUAUGCCU GGGGCCACAC
  RC99  AAGGUGGGGA UGACGUCAAG UCAGCAUGGC CUUUAUGCCU GGGGCCACAC
  RC11  AAGGUGGGGA UGACGUCAAG UCAGCAUGGC CUUUAUGCCU GGGGCCACAC
  RC73  AAGGUGGGGA UGACGUCAAG UCAGCAUGGC CUUUAUACCU GGGGCCACAC
  RC90  AAGGUGGGGA UGACGUCAAG UCAGCAUGGC CUUUAUGCCU GGGGCCACAC

[  1401                                                              1450  ]
SBR1024ACGUGCUACA AUGGCCGGUA CAAAGCGCUG CAAACCC.GU AAGGGGGAGC
SBR1015ACGUGCUACA AUGGCCGGUA CAAAGCGCUG CAAACCC.GU AAGGGGGAGC
  GC86  ACGUGCUACA AUGGCCGGUA CAAAGCGCUG CAAACCC.GU AAGGGGGAGC
SBR2046ACGUGCUACA AUGGCCGGUA CAAAGCGCUG CAAACCC.GU AAGGGGGAGC
  RC25  ACGUGCUACA AUGGCCGGUA CAAAGCGCUG CAAACCC.GU GAGGGGGAGC
  RC19  ACGUGCUACA AUGGCCGGUA CAAAGCGCUG CAAACCC.GU GAGGGGGAGC
SBR2016ACGUGCUACA AUGGCCGGUA CAAAGCGCUG CAAACCC.GU GAGGGGGAGC
  RC7   ACGUGCUACA AUGGCCGGUA CAAACGCUG CAAACCC.GU GAGGGGGAGC
  RC14  ACGUGCUACA AUGGCCGGUA UAAACGCUG CAAACCC.GU GAGGGGGAGC
  RC99  ACGUGCUACA AUGGCCGGUA CAAACGCUG CAAACCC.GU GAGGGGGAGC
  RC11  ACGUGCUACA AUGGCCGGUA CAAAGCGCUG CAAACCC.GU GAGGGGGAGC
  RC73  ACGUGCUACA AUGGCCGGUA CAAACGCUG CAAACCC.GU GAGGGGGAGC
  RC90  ACGUGCUACA AUGGCCGGUA CAAAACGCUG CAAACCC.GU GAGGGGGAGC

[  1451                                                              1500  ]
SBR1024CAAUCCCAAA AAACCGGCCU CAGUUCAGAU UGAGGUCUGC AACUCGACCU
SBR1015CAAUCGCAAA AAACCGGCCU CAGUUCAGAU UGAGGUCUGC AACUCGACCU
  GC86  CAAUCGCAAA AAACCGGCCU CAGUUCAGAU UGAGGUCUGC AACUCGACCU
SBR2046CAAUCGCAAA AAACCGGCCU CAGUUCAGAU UGAGGUCUGC AACUCGACCU
  RC25  CAAUCGCAAA AAACCGGCCU CAGUUCAGAU UGAGGUCUGC AACUCGACCU
  RC19  CAAUCGCAAA AAACCGGCCU CAGUUCAGAU UGAGGUCUGC AACUCGACCU
SBR2016CAAUCGCAAA AAACCGGCCU CAGUUCAGAU UGAGGUCUGC AACUCGACCU
  RC7   CAAUCGCAAA AAACCGGCCU CAGUUCAGAU UGAGGUCUGC AACUCGACCU
  RC14  CAAUCGCAAA AAACCGGCCU CAGUUCAGAU UGAGGUCUGC AACUCGACCU
  RC99  CAAUCGCAAA AAACCGGCCU CAGUUCAGAU UGAGGUCUGC AACUCGACCU
  RC11  CAAUCGCAAA AAACCGGCCU CAGUUCAGAU UGAGGUCUGC AACUCGACCU
  RC73  CAAUCGCAAA AAACCGGCCU CAGUUCAGAU UGAGGUCUGC AACUCGACCU
  RC90  CAAUCGCAAA AAACCGGCCU CAGUUCANAU UGAGGUCUGC AACUCGACCU
```

Fig. 8J

```
[ 1501                                                                1550 ]
SBR1024 CAUGAAGGCG GAAUCGCUAG UAAUCCCGGA UCAG.CACGC CGGGGUGAAU
SBR1015 CAUGAAGGCG GAAUCGCUAG UAAUCCCGGA UCAG.CACGC CGGGGUGAAU
  GC86  CAUGAAGGCG GAAUCGCUAG UAAUCCCGGA UCAG.CACGC CGGGGUGAAU
SBR2046 CAUGAAGGCG GAAUCGCUAG UAAUCCCGGA UCAG.CACGC CGGGGUGAAU
  RC25  CAUGAAGGCG GAAUCGCUAG UAAUCGCGGA UCAG.CACGC CGCGGUGAAU
  RC19  CAUGAAGGCG GAAUCGCUAG UAAUCGCGGA UCAG.CACGC CGCGGUGAAU
SBR2016 CAUGAAGGCG GAAUCGCUAG UAAUCGCGGA UCAG.CACGC CGCGGUGAAU
  RC7   CAUGAAGGCG GAAUCGCUAG UAAUCGCGGA UCAG.CACGC CGCGGUGAAU
  RC14  CAUGAAGGCG GAAUCGCUAG UAAUCGCGGA UCAG.CACGC CGCGGUGAAU
  RC99  CAUGAAGGCG GAAUCGCUAG UAAUCGCGGA UCAG.CACGC CGCGGUGAAU
  RC11  CAUGAAGGCG GAAUCGCUAG UAAUCGCGGA UCAG.CACGC CGCGGUGAAU
  RC73  CAUGAAUGCG GAAUCGCUAG UAAUCGCGGA UCAG.CACGC CGCGGUGAAU
  RC90  CAUGAAUGCG GAAUCGCUAG UAAUCGCGGA UCAG.CACGC CGCGGUGAAU

[ 1551                                                                1600 ]
SBR1024 ACGUUCCCGG GCCUUGUACA CACCGCCCGU CACACCACGA AAGUUUGUUG
SBR1015 ACGUUCCCGG ACCUUGUACA CACCGCCCGU CACACCACGA AAGUUUGUUG
  GC86  ACGUUCCCGG GCCUUGUACA CACCGCCCGU CACACCACGA AAGUUUGUUG
SBR2046 ACGUUCCCGG GCCUUGUACA CACCGCCCGU CACACCACGA AAGUUUGUUG
  RC25  ACGUUCCCGG GCCUUGUACA CACCGCCCGU CACACCACGA AAGCCUGUUG
  RC19  ACGUUCCCGG GCCUUGUACA CACCGCCCGU CACACCACGA AAGCCUGUUG
SBR2016 ACGUUCCCGG GCCUUGUACA CACCGCCCGU CACACCACGA AAGCCUGUUG
  RC7   ACGUUCCCGG GCCUUGUGCA CACCGCCCGU CACACCACGA AAGCCUGUUG
  RC14  ACGUUCCCGG GCCUUGUACA CACCGCCCGU CACACCACGA AAGCCUGUUG
  RC99  ACGUNCCCGG GCCUUGUACA CACCGCCCGU CACACCACGA AAGCCUGUUG
  RC11  ACGUNCCCGG GCCUUGUACA CACCGCCCGU CACACCACGA AAGCCUGUUG
  RC73  ACGUNCCCGG GCCUUGUACA CACCGCCCGU CACACCACGA AAGCCUGUUG
  RC90  ACGUNCCCGG GCCUUGUACA CGCCGCCCGU CACACCACGA AAGCCUGUUG

[ 1601                                                                1650 ]
SBR1024 UACCUGAAGU CGUUGGCGCC AACC...... GCAA...... GGAGGCAGAC
SBR1015 UACCUGAAGU CGUUGGCGCC AACC...... GCAA...... GGAG------
  GC86  UACCUGAAGU CGUUGGCGCC AACC...... GCAA...... GGGGGCAGAC
SBR2046 UACCUGAAGU CGUUGGCGCC AACC...... GCAA...... GGAGGCAGAC
  RC25  UACCUGAAGU CGCCCAAGCC AACC...... GCAA...... GGAGGCAGGC
  RC19  UACCUGAAGU CGCCCAAGCC AACC...... GCAA...... GGAGGCAGGC
SBR2016 UACCUGAAGU CGCCCAAGCC AACC...... GCAA...... GGAGGCAGGC
  RC7   UACCUGAAGU CGCCCAAGCC AACC...... GCAA...... GGAGGCAGGC
  RC14  UACCUGAAGU CGCCCAAGCC AACC...... GCAA...... GGAGGCAGGC
  RC99  UACCUGAAGU CGCCCAAGCC AACC...... GCAA...... GAAGGCAGGC
  RC11  UACCUGAAGU CGCCCAAGCC AACC...... GCAA...... GGAGGCAGGC
  RC73  UACCUGAAGU CGCCCAAGCC AACC...... GCAA...... GGAGGCAGGC
  RC90  UACCUGAAGU CGCCCAAGCC AACC...... GCAA...... GGAGGCANGC
```

*Fig. 8K*

```
[  1651                                                                    1700 ]
SBR1024GCCCACGGUA UGACCGAUGA UUGGG----- ---------- ----------
SBR1015---------- ---------- ---------- ---------- ----------
  GC86   GCCCACGGUA UGACCGAUGA UUGGGGUGAA GUCGUAACAA GGUAACCGUA
SBR2046GCCCACGGUA UGACCGAUGA UUGGGG---- ---------- ----------
  RC25   GCCCACGGUA UGGCCCGUGA UUGGGGUGAA GUCGUAACAA GGUAACCGUA
  RC19   GCCCACGGUA UGGCCGGUGA UUGGGGUGAA GUCCUAACA- ----------
SBR2016GCCCACGGUA UGGC------ ---------- ---------- ----------
  RC7    GCCCACGGUA UGGCCG---- ---------- ---------- ----------
  RC14   GCCCACGGUA UGGCCGGUGA U--------- ---------- ----------
  RC99   GCCCACGGUA UGGCCGGUGA ---------- ---------- ----------
  RC11   GCCCACGGUA UGGCCGGUGA UGGGG----- ---------- ----------
  RC73   GCCCACGGUA UGGCCGGUGA UGGGG----- ---------- ----------
  RC90   GCCCACGGUA UGGCCGGUGA UG...----- ---------- ----------

[  1701                                                                    1750 ]
SBR1024---------- ---------- ---------- ---------- ----------
SBR1015---------- ---------- ---------- ---------- ----------
  GC86   AUC------ ---------- ---------- ---------- ----------
SBR2046---------- ---------- ---------- ---------- ----------
  RC25   AA------- ---------- ---------- ---------- ----------
  RC19   ---------- ---------- ---------- ---------- ----------
SBR2016---------- ---------- ---------- ---------- ----------
  RC7    ---------- ---------- ---------- ---------- ----------
  RC14   ---------- ---------- ---------- ---------- ----------
  RC99   ---------- ---------- ---------- ---------- ----------
  RC11   ---------- ---------- ---------- ---------- ----------
  RC73   ---------- ---------- ---------- ---------- ----------
  RC90   ---------- ---------- ---------- ---------- ----------
  ;
```

Fig. 8L

SEQUENCE LISTING

<160> NUMBER OF SEQ ID NOS: 62

<210> SEQ ID NO 1
<211> LENGTH: 1428
<212> TYPE: DNA
<213> ORGANISM: Nitrospira

```
<220> FEATURE:
<221> NAME/KEY: misc_feature
<222> LOCATION: (1)...(1428)
<223> OTHER INFORMATION: n = A,T,C or G

<400> SEQUENCE: 1
caagtcgagc gagaagacgt agcaatacgt ttgtaaagcg gcgaacgggt gaggaataca     60
tgggtaacct accttcgagt ggggaataac tagccgaaag gttagctaat accgcatacg    120
actcctggtc tgcggatcgg gagagaaagc gataccgtgg gtatcgcgct cttggatggg    180
ctcatgtcct atcagcttgt tggtgaggta acggctcacc aaggcttcga cgggtagctg    240
gtctgagagg acgatcagcc acactggcac tgcgacacgg ccagactcc tacgggaggc     300 agcagtaagg aatattgcgc aatgggcgac agcctgacgc agcnacgccg cgtgggggat    360
gaaggtcttc ggattgtaaa ccccttcgg cagggaagat ggaacgggta accgttcgga     420
cggtacctgc agaagcagcc acgctaact tcgtgccagc agccgcggta atacgaaggt     480
ggcaagcgtt gttcggattt actgggcgta cagggagcgt aggcggttgg gtaagccctc    540
cgtgaaatct ccgggcctaa cccggaaagt gcggagggga ctgctcggct agaggatggg    600
agaggagcgc ggaattcccg gtgtagcggt gaaatgcgta gagatcggga ggaaggccgg    660
tggcgaaggc ggcgctctgg aacatttctg acgctgaggc tcgaaagcgt ggggagcaaa    720
caggattaga taccctggta gtccacgcct taaacgatgg atactaagtg tcggcgggtt    780
accgccggtg ccgcagctaa cgcattaagt atcccgcctg ggaagtacgg ccgcaaggtt    840
gaaactcaaa ggaattgacg ggggcccgca caagcggtgg agcatgtggt ttaattcgac    900
gcaacgcgaa gaaccttacc caggctggac atgcaggtag tagaagggtg aaagcctaac    960
gaggtagcaa taccatcctg ctcaggtgct gcatggctgt cgtcagctcg tgccgtgagg   1020
tgttgggtta agtcccgcaa cgagcgcaac ccctgtcttc agttaccaac gggtcatgcc   1080
gggaactctg gagagactgc ccaggagaac ggggaggaag gtggggatga cgtcaagtca   1140
gcatggcctt tatgcctggg ccacacacg tgctacaatg gccggtacaa agcgctgcaa     1200
acccgtaagg gggagccaat cccaaaaaac cggcctcagt tcagattgag gtctgcaact   1260
cgacctcatg aaggcggaat cgctagtaat cccggatcag cacgccgggg tgaatacgtn   1320
cccgggcctt gtacacaccg cccgtcacac cacgaaagtt tgttgtacct gaagtcgttg   1380
gcgccaaccg caaggaggca gacgcccacg gtatgaccga tgattggg                1428

<210> SEQ ID NO 2
<211> LENGTH: 1407
<212> TYPE: DNA
<213> ORGANISM: Nitrospira
<220> FEATURE:
<221> NAME/KEY: misc_feature
<222> LOCATION: (1)...(1407)
<223> OTHER INFORMATION: n = A,T,C or G

<400> SEQUENCE: 2
taatacatgc aagtcgagcg agaagacgta gcaatacgtt tgtaaagcgg cgaacgggtg     60
aggaatacat gggtagccta ccctcgagtg gggaataact aaccgaaagg ttagctaata    120 ccgcatacg ctcctggtct gcggatcggg agagaaagcg ataccgtggg tatcgcgctc     180
ttggatgggc tcatgtccta tcagcttgtt ggtgaggtaa cggctcacca aggcttcgac    240
gggtagctgg tctgagagga cgatcagcca cactggcact gcgacacggg ccagactcct    300
acgggaggca gcagtaagga atattgcgca atgggcgaca gcctgacgca gcnacgccgc    360
```

-continued

```
gtgggggatg aaggtcttcg gattgtaaac cccttccggc agggaagatg gaacgggtaa      420
ccgttcggac ggtacctgca gaagcagcca cggctaactt cgtgccagca gccgcggtaa      480
tacgaaggtg gcaagcgttg ttcggattta ctgggcgtac agggagcgta ggcggttggg      540
taagccctcc gtgaaatctc cgggcctaac ccggaaagtg cggaggggac tgctcggcta      600
gaggatggga gaggagcgcg gaattccgg tgtagcggtg aaatgcgtag agatcgggag       660
gaaggccggt ggcgaaggcg cgctctgga acatttctga cgctgaggct cgaaagcgtg       720
gggagcaaac aggattagat accctggtag tccacgcctt aaacgatgga tactaagtgt      780
cggcgggtta ccgccggtgc cgcagctaac gcattaagta tcccgcctgg gaagtacggc      840
cgcaaggttg aaactcaaag gaattgacgg gggcccgcac aagcggtgga gcatgtggtt      900
taattcgacg caacgcgaag aaccttaccc aggctggaca tgcaggtagt agaagggtga      960
aagcctaacg aggtagcaat accatcctgc tcaggtgctg catggctgtc gtcagctcgt     1020
gccgtgaggt gttgggttaa gtcccgcaac gagcgcaacc cctgtcttca gttaccaacg     1080
ggtcatgccg ggaactctgg agagactgcc aggagaacg ggggaggaag gtggggatga      1140
cgtcaagtca gcatggcctt tatgcctggg gccacacacg tgctacaatg gccggtacaa     1200
agcgctgcaa acccgtaagg gggagccaat cgcaaaaaac cggcctcagt tcagattgag     1260
gtctgcaact cgacctcatg aagcggaat cgctagtaat cccggatcag cacgccgggg      1320
tgaatacgtn cccggacctt gtacacaccg cccgtcacac cacgaaagtt gttgtacct     1380 gaagtcgttg gcgccaaccg caaggag                                         1407
```

<210> SEQ ID NO 3
<211> LENGTH: 1500
<212> TYPE: DNA
<213> ORGANISM: Nitrospira
<220> FEATURE:
<221> NAME/KEY: misc_feature
<222> LOCATION: (1)...(1500)
<223> OTHER INFORMATION: n = A,T,C or G

<400> SEQUENCE: 3

```
ttgatcctgg ctcagaacga acgctggcgg cgcgcctaat acatgcaagt cgagcgagaa       60
gacgtagcaa tacgttttgta aagcggcgaa cgggtgagga atacatgggt aacctaccct     120
cgagtgggga ataactagcc gaaaggttag ctaataccgc atacgactcc tggtctgcgg      180
atcgggagag aaagcgatac cgtgggtatc gcgctcttgg atgggctcat gtcctatcag      240
cttgttggtg aggtaacggc tcaccaaggc ttcgacgggt agctggtctg agaggacgat      300
cagccacact ggcactgcga cacgggccag actcctacgg gaggcagcag taaggaatat      360
tgcgcaatgg gcgacagcct gacgcagcna cgccgcgtgg gggatgaagg tcttcggatt      420
gtaaacccct tcggcaggg aagatggaac gggtaaccgt tcggacggta cctgcagaag      480
cagccacggc taacttcgtg ccagcagccg cggtaatacg aaggtggcaa gcgttgttcg      540
gatttactgg gcgtacaggg agcgtaggcg gttgggtaag ccctccgtga aatctccggg      600
cctaacccgg aaagtgcgga gggactgct cggctagagg atgggagagg agcgcggaat       660
tcccggtgta gcggtgaaat gcgtagagat cgggaggaag gccggtggcg aaggcggcgc     720
tctggaacat ttctgacgct gaggctcgaa agcgtgggga gcaaacagga ttagataccc     780
tggtagtcca cgccttaaac gatggatact aagtgtcggc gggttaccgc cggtgccgca     840
gctaacgcat taagtatccc gcctgggaag tacgccgcgca aggttgaaac tcaaaggaat     900 tgacggggc ccgcacaagc ggtggagcat gtggtttaat tcgacgcaac gcgaagaacc      960
```

```
ttacccaggc tggacatgca ggtagtagaa gggtgaaagc ctaacgaggt agcaacacca    1020
tcctgctcag gtgctgcatg gctgtcgtca gctcgtgccg tgaggtgttg ggttaagtcc    1080
cgcaacgagc gcaacccctg tcttcagtta ccaacgggtc atgccgggaa ctctggagag    1140
actgcccagg agaacgggga ggaaggtggg gatgacgtca agtcagcatg gcctttatgc    1200
ctggggccac acacgtgcta caatggccgg tacaaagcgc tgcaaacccg taaggggag     1260 ccaatcgcaa aaaccggcc tcagttcaga ttgaggtctg caactcgacc tcatgaaggc    1320
ggaatcgcta gtaatcccgg atcagcacgc cggggtgaat acgtncccgg gccttgtaca    1380
caccgcccgt cacaccacga aagtttgttg tacctgaagt cgttggcgcc aaccgcaagg    1440
gggcagacgc ccacggtatg accgatgatt ggggtgaagt cgtaacaagg taccgtaac    1500
```

<210> SEQ ID NO 4
<211> LENGTH: 1420
<212> TYPE: DNA
<213> ORGANISM: Nitrospira
<220> FEATURE:
<221> NAME/KEY: misc_feature
<222> LOCATION: (1)...(1420)
<223> OTHER INFORMATION: n = A,T,C or G

<400> SEQUENCE: 4

```
cgagaagacg tagcaatacg tttgtaaagc ggcgaacggg tgaggaatac atgggtaacc     60
taccctcgag tggggaataa ctaaccgaaa ggttagctaa taccgcatac ggctcctggt    120
ctgcggatcg ggagagaaag cgataccgtg gtatcgcgc tcttggatgg gctcatgtcc     180
tatcagcttg ttggtgaggt aacggctcac caaggcttcg acgggtagct ggtctgagag    240
gacgatcagc cacactggca ctgcgacacg gccagactc ctacgggagg cagcagtaag     300
gaatattgcg caatgggcga cagcctgacg cagcgacgcc gcgttgggga tgaaagtctt    360
ccgattgtaa accccttttcc gcagggaaga tggaacgggt aaccgttcgg acggtacctg    420
cagaagcagc cacggctaac ttcgtgccag cagccgcggt aatacgaagg tggcaagcgt    480
tgttcggatt tactgggcgt acaggagcg taggcggttg ggtaagccct ccgtgaaatc     540
tccgggccta acccggaaag tgcggagggg actgctcggc tagaggatgg gagaggagcg    600
cggaattccc ggtgtagcgg tgaaatgcgt agagatcggg aggaaggccg gtggcgaagg    660
cggcgctctg gaacatttct gacgctgagg ctcgaaagcg tggggagcaa acaggattag    720
ataccctggt agtccacgcc ttaaacgatg gatactaagt gtcggcgggt taccgccggt    780
gccgcagcta acgcattaag tatcccgcct gggaagtacg gccgcaaggt tgaaactcaa    840
aggaattgac ggggccccgc acaagcggtg gagcatgtgg tttaattcga cgcaacgcga    900
agaaccttac ccaggcagga catgcaggta gtagaagggt gaaagcctaa cgaggtagca    960
ataccatcct gctcaggtgc tgcatggctg tcgtcagctc gtgccgtgag gtgttgggtt   1020
aagtcccgca acgagcgcaa cccctgtctt cagttaccaa cgggtcatgc cggaactct    1080 ggagagactg cccaggagaa cggggaggaa ggtggggatg acgtcaagtc agcatggcct    1140
ttatgcctgg ggccacacac gtgctacaat ggccggtaca aagcgctgca aacccgtaag    1200
ggggagccaa tcgcaaaaaa ccggcctcag ttcagattga ggtctgcaac tcgacctcat    1260
gaaggcggaa tcgctagtaa tcccggatca gcacgccggg gtgaatacgt ncccgggcct    1320
tgtacacacc gcccgtcaca ccacgaaagt ttgttgtacc tgaagtcgtt ggcgccaacc    1380
gcaaggaggc agacgcccac ggtatgaccg atgattgggg                          1420
```

<210> SEQ ID NO 5
<211> LENGTH: 1505
<212> TYPE: DNA
<213> ORGANISM: Nitrospira
<220> FEATURE:
<221> NAME/KEY: misc_feature
<222> LOCATION: (1)...(1505)
<223> OTHER INFORMATION: n = A,T,C or G

<400> SEQUENCE: 5

| | | | | | |
|---|---|---|---|---|---|
| agagtttgat | cctggctcag | aacgaacgct | ggcggcgcgc | ctaatacatg | caagtcgagc | 60 |
| gagaagacgt | agcaatacgt | tgtaaagcg | gcgaacgggt | gaggaataca | tgggtaatct | 120 |
| accatcgagt | ggggaataac | caaccgaaag | gttggctaat | accgcgtacg | cttctgagtc | 180 |
| ttcggttcg | gaaggaaagc | cgtactgtga | gtgcggcgct | ctttgatgag | ctcatgtcct | 240 |
| atcagcttgt | tggtagggta | acggcctacc | aaggctttga | cgggtagctg | gtctgagagg | 300 |
| acgatcagcc | acactggcac | tgcgacacgg | gccagactcc | tacgggaggc | agcagtaagg | 360 |
| aatattgcgc | aatgggcgaa | agcctgacgc | agcnacgccg | cgtgggggat | gaaggtcttc | 420 |
| ggattgtaaa | ccccttcgg | gagggaagat | ggagcgagca | atcgttcgga | cggtacctcc | 480 |
| agaagcagcc | acggccaact | tcgtgccagc | agccgcggta | atacgaaggt | ggcaagcgtt | 540 |
| gttcggattc | actgggcgta | cagggtgtgt | aggcggtttg | gtaagccttc | tgttaaagct | 600 |
| tcgggcccaa | cccggaaagc | gcagacggta | ctgccaggct | agagggtggg | agaggagcgc | 660 |
| ggaattcccg | gtgtagcgt | gaaatgcgta | gagatcggga | ggaaggccgg | tggcgaaggc | 720 |
| ggcgctctgg | aacatacctg | acgctgagac | acgaaagcgt | ggggagcaaa | caggattaga | 780 |
| taccctggta | gtccacgccc | taaactatgg | atactaagtc | tcggcgggtt | accgccggtg | 840 |
| ccgcagctaa | cgcattaagt | atcccgcctg | ggaagtacgg | ccgcaaggtt | gaaactcaaa | 900 |
| ggaattgacg | ggggcccgca | caagcggtgg | agcatgtggt | ttaattcgac | gcaacgcgaa | 960 |
| gaaccttacc | caggttggac | atgcacgtag | tagaaaggtg | aaagcctgac | gaggtagcaa | 1020 |
| taccagcgtg | ctcaggtgct | gcatggctgt | cgtcagctcg | tgccgtgagg | tgttgggtta | 1080 |
| agtcccgcaa | cgagcgcaac | ccctgctttc | agttgctacc | gggtcatgcc | gagcactctg | 1140 |
| aaaggactgc | ccaggataac | ggggaggaag | gtggggatga | cgtcaagtca | gcatggcctt | 1200 |
| tatgcctggg | gccacacacg | tgctacaatg | gccggtacaa | agcgctgcaa | acccgtgagg | 1260 |
| gggagccaat | cgcaaaaaac | cggcctcagt | tcagattgag | gtctgcaact | cgacctcatg | 1320 |
| aaggcggaat | cgctagtaat | cgcggatcag | cacgccgcgg | tgaatacgtn | cccgggcctt | 1380 |
| gtacacaccg | cccgtcacac | cacgaaagcc | tgttgtacct | gaagtcgccc | aagccaaccg | 1440 |
| caaggaggca | ggcgcccacg | gtatggcccg | tgattggggt | gaagtcgtaa | caaggtaacc | 1500 |
| gtaaa | | | | | | 1505 |

<210> SEQ ID NO 6
<211> LENGTH: 1441
<212> TYPE: DNA
<213> ORGANISM: Nitrospira
<220> FEATURE:
<221> NAME/KEY: misc_feature
<222> LOCATION: (1)...(1441)
<223> OTHER INFORMATION: n = A,T,C or G

<400> SEQUENCE: 6

| | | | | | |
|---|---|---|---|---|---|
| aagtcgagcg | agaaggtgta | gcaatacact | tgtaaagcgg | cgaacgggtg | aggaatacat | 60 |
| gggtaatcta | ccatcgagtg | ggggaataacc | agccgaaagg | ttggctaata | ccgcgtacgc | 120 |

-continued

```
ttccgagtct tcgggcttgg aaggaaagcc gcactgtgag tgcggcgctc tttgatgagc      180
tcatgtccta tcagcttgtt ggtagggtaa cggcctacca aggctttgac gggtagctgg      240
tctgagagga cgatcagcca cactggcact gcgacacggg ccagactcct acgggaggca      300
gcagtaagga atattgcgca atgggcgaaa gcctgacgca gcgacgccgc gtggggatg       360 aaggtcttcg gattgtaaac ccctttcggg agggaagatg gagccagcaa tcgttcggac      420
ggtacctcca gaagcagcca cggccaactt cgtgccagca gccgcggtaa tacgaaggtg      480
gcaagcgttg ttcggattca ctgggcgtac agggtgtgta ngcggtttgg taagccttct      540
gttaaagctt cgggcccaac ccggaaagcg cagagggtac tgccaggcta gagggtggga     600
gaggagcgcg gaattcccgg tgtagcggtg aaatgcgtag agatcgggag gaaggccggt     660
ggcgaaggcg gcgctctgga acatgcctga cgctgagaca cgaaagcgtg gggagcaaac     720
aggattagat accctggtag tccacgccct aaactatgga tactaagtgt cggcgggtta     780
ccgccggtgc cgcagctaac gcattaagta tcccgcctgg gaagtacggc cgcaaggttg     840
aaactcaaag gaattgacgg gggcccgcac aagcggtgga gcatgtggtt taattcgacg     900
caacgcgaag aaccttaccc aggttggaca tgcacgtagt agaaggtgaa agnctaacg     960 aggtagcaat accagcgtgc tcaggtgctg catggctgtc gtcagctcgt gccgtgaggt    1020
gttgggttaa gtcccgcaac gagcgcaacc cctgctttca gttgctaccg ggtcatgccg    1080
agcactctga aaggactgcc caggataacg gggaggaagg tggggatgac gtcaagtcag    1140
catggccttt atgcctgggg ccacacacgt gctacaatgg ccggtacaaa gcgctgcaaa    1200
cccgtgaggg ggagccaatc gcaaaaaacc ggcctcagtt cagattgagg tctgcaactc    1260
gacctcatga aggcggaatc gctagtaatc gcggatcagc acgccgcggt gaatacgtnc    1320
ccgggccttg tacaccgcc cgtcacacc acgaaagcct gttgtacctg aagtcgccca    1380
agccaaccgc aaggaggcag gcgcccacgg tatggccggt gattggggtg aagtcctaac    1440
a                                                                       1441
```

<210> SEQ ID NO 7
<211> LENGTH: 1426
<212> TYPE: DNA
<213> ORGANISM: Nitrospira
<220> FEATURE:
<221> NAME/KEY: misc_feature
<222> LOCATION: (1)...(1426)
<223> OTHER INFORMATION: n = A,T,C or G

<400> SEQUENCE: 7

```
taatacatgc aagtcgagcg agaaggtgta gcaatacact tgtaaagcgg cgaacgggtg       60
aggaatacat gggtaatcta ccatcgagtg gggaataacc aaccgaaagg ttggctaata      120
ccgcgtacgc ttctgagcct tcgtgttcgg aaggaaagcc gtactgtgag tgcggcgctc      180
tttgatgagc tcatgtccta tcagcttgtt ggtagggtaa cggcctacca aggctttgac      240
gggtagctgg tctgagagga cgatcagcca cactggcact gcgacacggg ccagactcct      300
acgggaggca gcagtaagga atattgcgca atgggcgaaa gcctgacgca gcnacgccgc      360 gtggggatg aaggtcttcg gattgtaaac ccctttcggg agggaagatg gagcgagcaa      420
tcgttcggac ggtacctcca gaagcagcca cggccaactt cgtgccagca gccgcggtaa     480
tacgaaggtg gcaagcgttg cttggattca ctgggcgtac agggtgtgta ggcggtttgg     540
taagccttct gttaaagctt cgggcccaac ccgaaaagcg cagagggtac tgccaggcta    600
```

-continued

```
gagggtggga gaggagcgcg gaattcccgg tgtagcggtg aaatgcgtag agatcgggag      660
gaaggccggt ggcgaaggcg gcgctctgga acatacctga cgctgagaca cgaaaacgtg      720
gggagcaaac aggattagat accctggtag tccacgccct aaactatgga tactaagtgt      780
cggcgggtta ccgccggtgc cgcagctaac gcattaagta tcccgcctgg gaggtacggc      840
cgcaaggttg aaactcaaag gaattgacgg gggcccgcac aagcggtgga gcttgtggtt      900
taattcgacg caacgcgaag aaccttaccc aggttggaca tgcacgtagt agaaaggtga      960
aagcctgacg aggtagcaat accagcgtgc tcaggtgctg catggctgtc gtcagctcgt     1020
gccgtgaggt gttgggttaa gtcccgcaac gagcgcaacc cctgctttca gttgctaccg     1080
ggtcatgccg agcactctga aaggactgcc caggataacg ggggaggaagg tggggatgac    1140 gtcaagtcag catggccttt atgcctgggg ccacacacgt gctacaatgg ccggtacaaa     1200
gcgctgcaaa cccgtgaggg ggagccaatc gcaaaaaacc ggcctcagtt cagattgagg     1260
tctgcaactc gacctcatga aggcggaatc gctagtaatc gcggatcagc acgccgcggt     1320
gaatacgtnc ccgggccttg tacacaccgc ccgtcacacc acgaaagcct gttgtacctg     1380
aagtcgccca agccaaccgc aaggaggcag gcgcccacgg tatggc                   1426
```

<210> SEQ ID NO 8
<211> LENGTH: 1429
<212> TYPE: DNA
<213> ORGANISM: Nitrospira
<220> FEATURE:
<221> NAME/KEY: misc_feature
<222> LOCATION: (1)...(1429)
<223> OTHER INFORMATION: n = A,T,C or G

<400> SEQUENCE: 8

```
taatacatgc aagtcgagcg agaaggtgta gcaatacact tgtaaagcgg cgaacgggtg       60
aggaatacat gggtaatcta ccatcgagtg gggaataacc aaccgaaagg ttggctaata      120
ccgcgtacgc ctccgagtct tcgggttcgg agggaaagct gcactgtgag tgtagcgctc      180
tttgatgagc tcatgtccta tcagcttgtt ggtagggtaa cggcctacca aggctttgac      240
gggtagctgg tctgagagga cgatcagcca cactggcact gcgacacggg ccagactcct      300
acgggaggca gcagtaagga atattgcgca atgggcgaaa gcctgacgca gcnacgccgc      360 gtggggatg aaggtcttcg gattgtaaac ccctttcggg agggaagatg agcgagcaa       420 tcgttcggac ggtacctcca gaagcagcca cggccaactt cgtgccagca gccgcggtaa     480
tacgaaggtg gcaagcgttg ttcggattca ctgggcgtac agggtgtgta ggcggtttgg     540
taagccttct gttaaagctt cgggcccaac ccggaaagcg caggggtac tgccaggcta     600 gagggtggga gaggagcgcg gaattcccgg tgtagcggtg aaatgcgtag agatcgggag      660
gaaggccggt ggcgaaggcg gcgctctgga acatacctga cgctgagaca cgaaagcgtg      720
gggagcaaac aggattagat accctggtag tccacgccct aagctatgga tactaagtgt      780
cggcgggtta ccgccggtgc cgcagccaac gcgttaagta tcccgcctgg gaagtacggc      840
cgcaaggttg aaactcaaag gaattgacgg gggcccgcac aagcggtgga gcatgtggtt      900
taattcgacg caacgcgaag aaccttaccc aggttggaca tgcacgtagt agaaaggtga      960
aagcctgacg aggtagcaat accagcgtgc tcaggtgctg catggctgtc gtcagctcgt     1020
gccgtgaggt gttgggttaa gtcccgcaac gagcgcaacc cctgctttca gttgctaccg     1080
ggtcatgccg agcactctga aaggactgcc caggataacg ggggaggaag gtggggatga     1140
cgtcaagtca gcatggcctt tatgcctggg gccacacacg tgctacaatg gccggtacaa     1200
```

| aacgctgcaa acccgtgagg gggagccaat cgcaaaaaac cggcctcagt tcagattgag | 1260 |
| gtctgcaact cgacctcatg aaggcggaat cgctagtaat cgcggatcag cacgccgcgg | 1320 |
| tgaatacgtn cccgggcctt gtgcacaccg cccgtcacac cacgaaagcc tgttgtacct | 1380 |
| gaagtcgccc aagccaaccg caaggaggca ggcgcccacg gtatggccg | 1429 |

<210> SEQ ID NO 9
<211> LENGTH: 1415
<212> TYPE: DNA
<213> ORGANISM: Nitrospira
<220> FEATURE:
<221> NAME/KEY: misc_feature
<222> LOCATION: (1)...(1415)
<223> OTHER INFORMATION: n = A,T,C or G

<400> SEQUENCE: 9

| cgagaaggtg tagcaataca cttgtaaagc ggcgaacggg tgaggaatac atgggtaatc | 60 |
| taccatcgag tggggaataa ccaaccgaaa ggttggctaa taccgcgtac gcctccgagt | 120 |
| cttcggttc ggagggaaag ctgcactgtg agtgtagcgc tctttgatga gctcatgtcc | 180 |
| tatcagcttg ttggtagggt aacggcctac caaggctttg acgggtagct ggtctgagag | 240 |
| gacgatcagc cacactggca ctgcgacacg gccagactc ctacggggagg cagcagtaag | 300 |
| gaatattgcg caatgggcga aagcctgacg cagcnacgcc gcgtggggga tgaaggtctt | 360 |
| cggattgtaa acccctttcg ggagggaaga tggagcgagc aatcgttcgg acggtacctc | 420 |
| cagaagcagc cacggccaac ttcgtgccag cagccgcggt aatacgaagg tggcaagcgt | 480 |
| tgttcggatt cactgggcgt acagggtgtg taggcggttt ggtaagcctt ctgttaaagc | 540 |
| ttcgggccca acccggaaag cgcagagggt actgccaggc tagagggtgg gagaggagcg | 600 |
| cggaattccc ggtgtagcgg tgaaatgcgt agagatcggg aggaaggccg gtggcgaagg | 660 |
| cggcgctctg gaacatacct gacgctgaga cacgaaagcg tggggagcaa acaggattag | 720 |
| ataccctggt agtccacgcc ctaaactatg gatactaagt gtcggcgggt taccgccggt | 780 |
| gccgcagcta acgcattaag tatcccgcct gggaagtacg gccgcaaggt tgaaactcaa | 840 |
| aggaattgac gggggcccgc acaagcggtg gagcatgtgg tttaattcga cgcaacgcga | 900 |
| agaaccttac ccaggttgga catgcacgta gtagaaaggt gaaagcctga cgaggtagca | 960 |
| ataccagcgt gctcaggtgc tgcatggctg tcgtcagctc gtgccgtgag gtgttgggtt | 1020 |
| aagtcccgca acgagcgcaa cccctgcttt cagttgctac cgggtcatgc cgagcactct | 1080 |
| gaaaggactg cccaggataa cggggaggaa ggtggggatg acgtcaagtc agcatggcct | 1140 |
| ttatgcctgg ggcacacac gtgctacaat ggccggtata aaacgctgca aacccgtgag | 1200 |
| ggggagccaa tcgcaaaaaa ccggcctcag ttcagattga ggtctgcaac tcgacctcat | 1260 |
| gaaggcggaa tcgctagtaa tcgcggatca gcacgccgcg gtgaatacgt ncccgggcct | 1320 |
| tgtacacacc gcccgtcaca ccacgaaagc ctgttgtacc tgaagtcgcc caagccaacc | 1380 |
| gcaaggaggc aggcgcccac ggtatggccg gtgat | 1415 |

<210> SEQ ID NO 10
<211> LENGTH: 1435
<212> TYPE: DNA
<213> ORGANISM: Nitrospira
<220> FEATURE:
<221> NAME/KEY: misc_feature
<222> LOCATION: (1)...(1435)
<223> OTHER INFORMATION: n = A,T,C or G

```
<400> SEQUENCE: 10
cctaatacat gcaagtcgat cgagaaggtg tagcaataca cttgtaaagc ggcgaacggg      60
tgaggaatac atgggtaatc taccatcgag tggggaataa ccaaccgaaa ggttggctaa     120
taccgcgtac gcctccgagt cttcgggttc ggagggaaag ctgcactgtg agtgtagcgc     180
tctttgatga gctcatgtcc tatcagcttg ttggtagggt aacggcctac caaggctttg     240
acgggtagct ggtctgagag gacgatcagc cacactggca ctgcgacacg gccagactc     300 ctacgggagg cagcagtaag gaatattgcg caatgggcga agcctgacg cagccacgcc     360 gcgtggggga tgaaggtctt cggattgtaa accccttcg ggagggaaga tggagcgagc     420
aatcgttcgg acggtacctc cagaagcagc acggccaac ttcgtgccag cagccgcggt     480
aatacgaagg tggcaagcgt tgttcggatt cactgggcgt acagggtgtg taggcggttt     540
ggtaagcctt ctgttaaagc ttcgggccca acccggaaag cgcagagggt actgccaggc     600
tagagggtgg gagaggagcg cggaattccc ggtgtagcgg tgaaatgcgt agagatcggg     660
aggaaggccg gtggcgaagg cggcgctctg aacatacct gacgctgaga cacgaaagcg     720
tggggagcaa acaggattag ataccctggt agtccacgcc ctaaactatg gatactaagt     780
gtcggcgggt taccgccggt gccgcagcta acgcattaag tatcccgcct gggaagtacg     840
gccgcaaggt tgaaactcaa aggaattgac ggggcccgc acaagcggtg gagcatgtgg     900
tttaattcga cgcaacgcga agaaccttac ccaggttgga catgcacgta gtagaaaggt     960
gaaagcctga cgaggtagca ataccagcgt gctcaggtgc tgcatggctg tcgtcagctc    1020
gtgccgtgag gtgttgggtt aagtcccgca acgagcgcaa ccctgctt cagttgctac    1080 cgggtcatgc cgagcactct gaaaggactg cccaggataa cggggaagga aggtggggat    1140
gacgtcaagt cagcatggcc tttatgcctg ggccacaca cgtgctacaa tggccggtac    1200
aaaacgctgc aaacccgtga gggggagcca atcgcaaaaa accggcctca gttcagattg    1260
aggtctgcaa ctcgacctca tgaaggcgga atcgctagta atcgcggatc agcacgccgc    1320
ggtgaatacg tncccgggcc ttgtacacac cgcccgtcac accacgaaag cctgttgtac    1380
ctgaagtcgc ccaagccaac cgcaagaagg caggcgccca cggtatggcc ggtga         1435

<210> SEQ ID NO 11
<211> LENGTH: 1437
<212> TYPE: DNA
<213> ORGANISM: Nitrospira
<220> FEATURE:
<221> NAME/KEY: misc_feature
<222> LOCATION: (1)...(1437)
<223> OTHER INFORMATION: n = A,T,C or G

<400> SEQUENCE: 11
aatacatgca gtcgatcga gaaggtgtag caatacactt gtaaagcggc gaacgggtga      60
ggaatacatg ggtaatctac catcgagtgg ggaataacca accgaaaggt tggctaatac     120
cgcgtacgcc tccgagtctt cgggttcgga gggaaagctg cactgtgagt gtagcgctct     180 tgatgagct catgtcctat cagcttgttg gtagggtaac ggcctaccaa ggctttgacg     240
ggtagctggt ctgagaggac gatcagccac actggcactg cgacacgggc cagactccta     300
cgggaggcag cagtaaggaa tattgcgcaa tgggcgaaag cctgacgcag ccacgccgcg     360 tggggatga aggtcttcgg attgtaaacc cctttcggga gggaagatgg agcgagcaat    420 cgttcgacg gtacctccag aagcagccac ggccaacttc gtgccagcag ccgcggtaat    480
acgaaggtgg caagcgttgt tcggattcac tgggcgtaca gggtgtgtag gcggtttggt    540
```

```
aagccttctg ttaaagcttc gggcccaacc cggaaagcgc agagggtact gccaggctag    600
agggtgggag aggagcgcgg aattcccggt gtagcggtga aatgcgtaga gatcgggagg    660
aaggccggtg gcgaaggcgg cgctctggaa catacctgac gctgagacac gaaagcgtgg    720
ggagcaaaca ggattagata ccctggtagt ccacgcccta aactatggat actaagtgtc    780
ggcgggttac cgccggtgcc gcagctaacg cattaagtat cccgcctggg aagtacggcc    840
gcaaggttga aactcaaagg aattgacggg ggcccgcaca gcggtggag catgtggttt     900 aattcgacgc aacgcgaaga accttaccca ggttggacat gcacgtagta naaggtgaa     960 agcctgacga ggtagcaata ccagcgtgct caggtgctgc atggctgtct tcagctcgtg   1020
ccgtgaggtg ttgggttaag tcccgcaacg agcgcaaccc ctgctttcag ttgctaccgg   1080
gtcatgccga acactctgaa aggactgccc aggataacgg ggaaggaagg tggggatgac   1140
gtcaagtcag catggccttt atgcctgggg ccacacacgt gctacaatgg ccggtacaaa   1200
gcgctgcaaa cccgtgaggg ggagccaatc gcaaaaaacc ggcctcagtt cagattgagg   1260
tctgcaactc gacctcatga aggcggaatc gctagtaatc gcggatcagc acgccgcggt   1320
gaatacgtnc ccgggccttg tacacaccgc ccgtcacacc acgaaagcct gttgtacctg   1380
aagtcgccca agccaaccgc aaggaggcag gcgcccacgg tatggccggt gatgggg     1437
```

<210> SEQ ID NO 12  
<211> LENGTH: 1437  
<212> TYPE: DNA  
<213> ORGANISM: Nitrospira  
<220> FEATURE:  
<221> NAME/KEY: misc_feature  
<222> LOCATION: (1)...(1437)  
<223> OTHER INFORMATION: n = A,T,C or G

<400> SEQUENCE: 12

```
aatacatgca agtcgatcga naaggtgtag caatacactt gtaaagcggc gaacgggtga     60
ggaatacatg gtaatctac catcgagtgg ggaataacca accgaaaggt tggctaatac     120
cgcgtacgcc tccgagtctt cgggttcgga gggaaagctg cactgtgagt gtagcgctct    180
ttgatgagct catgtcctat cagcttgttg gtagggtaac ggcctaccaa ggctttgacg    240
ggtatctggt ctgagaggac gatcagccac actggcactg cgacacgggc cagactccta    300
cgggaggcag cagtaaggaa tattgcgcaa tgggcgaaac ccngacgcag ccacgccgcg    360
tgggggatga aggtcttcgg attgtaaacc cctttcggga gggaagatgg aacgagcaat    420 cgttcgacg gtacctccag aagcagccac ggccaacttc gtgccagcag ccgcggtaat    480
acgaaggtgg caagcgttgt tcggattcac tgggcgtaca gggtgtgtag gcggtttggt    540
aagccttctg ttaaagcttc gggcccaacc cggaaagcgc agagggtact gccaggctag    600
agggtgggag aggagcgcgg aattcccggt gtagcggtga aatgcgtaga gatcgggagg    660
aaggccggtg gcgaaggcgg cgctctggaa catacctgac gctgagacac gaaagcgtgg    720
ggngcaaaca ggattagata ccctggtagt ccacgcccta aactatggat actaagtgtc    780
ggcgggttac cgccggtgcc gcagctaacg cattaagtat cccgcctggg aagtacggcc    840
gcaaggttga aactcaaagg gattgacggg ggcccgcaca gcggtgggg catgtggttt     900 aattcgacgc aacgcgaaga accttaccca ggttggacat gcacgtagtn gaaaggtgaa     960
agcctgacga ggtagcaata ccagcgtgct caggtgctgc atggctgtcg tcagctcgtg   1020
ccgtgaggtg ttgggttaag tcccgcaacg agcgcaaccc ctgctttcag ttgctaccgg   1080
```

```
gtcatgccga acactctgaa aggactgccc aggataacgg ggaaggaagg tggggatgac    1140
gtcaagtcag catggccttt atacctgggg ccacacacgt gctacaatgg ccggtacaaa    1200
acgctgcaaa cccgtgaggg ggagccaatc gcaaaaaacc ggcctcagtt cagattgagg    1260
tctgcaactc gacctcatga atgcggaatc gctagtaatc gcggatcagc acgccgcggt    1320
gaatacgtnc ccgggccttg tacacaccgc ccgtcacacc acgaaagcct gttgtacctg    1380
aagtcgccca agccaaccgc aaggaggcag gcgcccacgg tatggccggt gatgggg      1437
```

<210> SEQ ID NO 13
<211> LENGTH: 1435
<212> TYPE: DNA
<213> ORGANISM: Nitrospira
<220> FEATURE:
<221> NAME/KEY: misc_feature
<222> LOCATION: (1)...(1435)
<223> OTHER INFORMATION: n = A,T,C or G

<400> SEQUENCE: 13

```
taatacatgc aagtcgatcg anaaggtgta gcaatacact tgtaaagcgg cgaacgggtg     60
aggaatacat gggtaatcta ccatcgagtg gggaataacc aaccgaaagg ttggctaata    120
ccgcgtacgc ttccgagtct tcgggcttgg aaggaaagcc gcactgtgag tgcggcgctc    180
tttgatgagc tcatatccta tcancttgtt ggtagggtaa cggcctacca aggctttgac    240
gggtatctgg tctgagagga cgatcagcca cactggcact gcgacacggg ccagactcct    300
acgggaggca gcagtaagga atattgcgca atgggcgaaa cccngacgca gccacgccgc    360 gtggggatg  aaggtcttcg gattgtaaac ccctttcggg agggaagatg gaacgagcaa    420
tcgttcggac ggtacctcca gaagcagcca cggccaactt cgtgccagca gccgcggtaa    480
tacgaaggtg gcaagcgttg ttcggattca ctgggcgtac agggtgtgta ggcggtttgg    540
taagccttct gttaaagctt cgggcccaac ccggaaagcg cagagggtac tgccaggcta    600
gagggtggga gaggagcgcg gaattcccgg tgtagcggtg aaatgcgtag agatcgggag    660
gaaggccggt ggcgaaggcg cgctctgga  acatacctga cgctcagaca cgaaagcgtg    720
gggagcaaac aggattagat accctggtag tccacgccct aaactatgga tactaagtgt    780
cggcgggtta ccgccggtgc cgcagctaac gcattaagta tcccgcctgg gaagtacggc    840
cgcaaggttg aaactcaaag gaattgacgg gggcccgcac aagcggtgga gcatgtggtt    900
taattcgacg caacgcgaag aaccttaccc aggttggaca tgcacgtagt agaaaggtga    960
aagcctgacg aggtagcaat accagcgtgc tcaggtgctg catggctgtc gtcagctcgt   1020
gccgtgaggt gttgggttaa gtcccgcaac gagcgcaacc cctgctttca gttgctgccg   1080
ggtcatgccg aacactctga aaggactgcc caggataacg gggaaggaag gtggggatga   1140
cgtcaagtca gcatggcctt tatgcctggg gccacacacg tgctacaatg gccggtacaa   1200
aacgctgcaa acccgtgagg gggagccaat cgcaaaaaac cggcctcagt tcanattgag   1260
gtctgcaact cgacctcatg aatgcggaat cgctagtaat cgcggatcag cacgccgcgg   1320
tgaatacgtn cccgggcctt gtacacgccg cccgtcacac cacgaaagcc tgttgtacct   1380
gaagtcgccc aagccaaccg caaggaggca ngcgcccacg gtatggccgg tgatg        1435
```

<210> SEQ ID NO 14
<211> LENGTH: 18
<212> TYPE: DNA
<213> ORGANISM: Artificial Sequence
<220> FEATURE:
<223> OTHER INFORMATION: Consensus sequence of 16s rDNA sequences of nitrite oxidisers from various bacterial phyla

<400> SEQUENCE: 14
cgggagggaa gatggagc					18

<210> SEQ ID NO 15
<211> LENGTH: 20
<212> TYPE: DNA
<213> ORGANISM: Artificial Sequence
<220> FEATURE:
<223> OTHER INFORMATION: Consensus sequence of 16s rDNA sequence of
      nitrite oxidisers from various bacterial phyla

<400> SEQUENCE: 15
ccaacccgga aagcgcagag					20

<210> SEQ ID NO 16
<211> LENGTH: 18
<212> TYPE: DNA
<213> ORGANISM: Artificial Sequence
<220> FEATURE:
<223> OTHER INFORMATION: Consensus sequence of rDNA sequences from
      nitrite oxidisers from various bacterial phyla

<400> SEQUENCE: 16
agcctggcag taccctct					18

<210> SEQ ID NO 17
<211> LENGTH: 18
<212> TYPE: DNA
<213> ORGANISM: Nitrococcus mobilis

<400> SEQUENCE: 17
cagccgggag gaaaagca					18

<210> SEQ ID NO 18
<211> LENGTH: 18
<212> TYPE: DNA
<213> ORGANISM: Magnetobacterium bavaricum

<400> SEQUENCE: 18
tgtagggaaa gatgatga					18

<210> SEQ ID NO 19
<211> LENGTH: 18
<212> TYPE: DNA
<213> ORGANISM: Nitrobacter hamburgensis

<400> SEQUENCE: 19
tgtgcgggaa gataatga					18

<210> SEQ ID NO 20
<211> LENGTH: 18
<212> TYPE: DNA
<213> ORGANISM: Nitrospina gracilis

<400> SEQUENCE: 20
cgggtgggaa gaacaaaa					18

<210> SEQ ID NO 21
<211> LENGTH: 18
<212> TYPE: DNA
<213> ORGANISM: Nitrospira marina

<400> SEQUENCE: 21

-continued

```
catgaggaaa gataaagt                                              18

<210> SEQ ID NO 22
<211> LENGTH: 18
<212> TYPE: DNA
<213> ORGANISM: Nitrospira

<400> SEQUENCE: 22
cggcagggaa gatggaac                                              18

<210> SEQ ID NO 23
<211> LENGTH: 18
<212> TYPE: DNA
<213> ORGANISM: Nitrospira

<400> SEQUENCE: 23
cgggagggaa gatggagc                                              18

<210> SEQ ID NO 24
<211> LENGTH: 18
<212> TYPE: DNA
<213> ORGANISM: Nitrospira

<400> SEQUENCE: 24
ccgcagggaa gatggaac                                              18

<210> SEQ ID NO 25
<211> LENGTH: 18
<212> TYPE: DNA
<213> ORGANISM: Nitrospira

<400> SEQUENCE: 25
cgggagggaa gatggaac                                              18

<210> SEQ ID NO 26
<211> LENGTH: 18
<212> TYPE: DNA
<213> ORGANISM: Nitrobacter

<400> SEQUENCE: 26
cgtgcgggaa gataatga                                              18

<210> SEQ ID NO 27
<211> LENGTH: 18
<212> TYPE: DNA
<213> ORGANISM: Nitrospira

<400> SEQUENCE: 27
cggcagggaa gatggaac                                              18

<210> SEQ ID NO 28
<211> LENGTH: 18
<212> TYPE: DNA
<213> ORGANISM: Nitrospira moscoviensis

<400> SEQUENCE: 28
cgggagggaa gatggacg                                              18

<210> SEQ ID NO 29
<211> LENGTH: 20
<212> TYPE: DNA
<213> ORGANISM: Nitrococcus mobilis
```

-continued

<210> SEQ ID NO 29

<400> SEQUENCE: 29
tcaacctggg aattgcatcc                    20

<210> SEQ ID NO 30
<211> LENGTH: 20
<212> TYPE: DNA
<213> ORGANISM: Magnetobacterium bavaricum

<400> SEQUENCE: 30
tcaacccggg aattgccttg                    20

<210> SEQ ID NO 31
<211> LENGTH: 20
<212> TYPE: DNA
<213> ORGANISM: Nitrobacter hamburgensis

<400> SEQUENCE: 31
tcaactccag aactgccttt                    20

<210> SEQ ID NO 32
<211> LENGTH: 20
<212> TYPE: DNA
<213> ORGANISM: Nitrospina gracilis

<400> SEQUENCE: 32
tcaaccgtgg aattgcgttt                    20

<210> SEQ ID NO 33
<211> LENGTH: 20
<212> TYPE: DNA
<213> ORGANISM: Nitrospina marina

<400> SEQUENCE: 33
ttaaccggga aggtcgaga                     20

<210> SEQ ID NO 34
<211> LENGTH: 20
<212> TYPE: DNA
<213> ORGANISM: Nitrospira

<400> SEQUENCE: 34
ctaacccgga aagtgcggag                    20

<210> SEQ ID NO 35
<211> LENGTH: 20
<212> TYPE: DNA
<213> ORGANISM: Nitrospira

<400> SEQUENCE: 35
ccaacccgaa aagcgcagag                    20

<210> SEQ ID NO 36
<211> LENGTH: 20
<212> TYPE: DNA
<213> ORGANISM: Nitrospira

<400> SEQUENCE: 36
ccaacccgga aagcgcagag                    20

<210> SEQ ID NO 37
<211> LENGTH: 20
<212> TYPE: DNA
<213> ORGANISM: Nitrobacter

```
<400> SEQUENCE: 37
tcaactccag aactgccttt                                                    20

<210> SEQ ID NO 38
<211> LENGTH: 20
<212> TYPE: DNA
<213> ORGANISM: Nitrospira moscoviensis

<400> SEQUENCE: 38
ccaacccgga aagcgcagag                                                    20

<210> SEQ ID NO 39
<211> LENGTH: 18
<212> TYPE: DNA
<213> ORGANISM: Nitrococcus mobilis

<400> SEQUENCE: 39
agccaaacag tatcggat                                                      18

<210> SEQ ID NO 40
<211> LENGTH: 18
<212> TYPE: DNA
<213> ORGANISM: Magnetobacterium bavaricum

<400> SEQUENCE: 40
agttaaacag ttttcaag                                                      18

<210> SEQ ID NO 41
<211> LENGTH: 18
<212> TYPE: DNA
<213> ORGANISM: Nitrobacter hamburgensis

<400> SEQUENCE: 41
agaccttcag tatcaaag                                                      18

<210> SEQ ID NO 42
<211> LENGTH: 18
<212> TYPE: DNA
<213> ORGANISM: Nitrospina gracilis

<400> SEQUENCE: 42
agccgaatag tttcaaac                                                      18

<210> SEQ ID NO 43
<211> LENGTH: 18
<212> TYPE: DNA
<213> ORGANISM: Nitrospina marina

<400> SEQUENCE: 43
agctgaatag ttcctctc                                                      18

<210> SEQ ID NO 44
<211> LENGTH: 18
<212> TYPE: DNA
<213> ORGANISM: Nitrospira

<400> SEQUENCE: 44
agccgagcag tccctcc                                                       18

<210> SEQ ID NO 45
<211> LENGTH: 18
<212> TYPE: DNA
```

<213> ORGANISM: Nitrospira

<400> SEQUENCE: 45
agcctggcag taccctct        18

<210> SEQ ID NO 46
<211> LENGTH: 18
<212> TYPE: DNA
<213> ORGANISM: Nitrospira

<400> SEQUENCE: 46
agcctggcag taccccct        18

<210> SEQ ID NO 47
<211> LENGTH: 18
<212> TYPE: DNA
<213> ORGANISM: Nitrospira

<400> SEQUENCE: 47
agcctggcag taccgtct        18

<210> SEQ ID NO 48
<211> LENGTH: 18
<212> TYPE: DNA
<213> ORGANISM: Nitrobacter

<400> SEQUENCE: 48
agatcctcag tatcaaag        18

<210> SEQ ID NO 49
<211> LENGTH: 18
<212> TYPE: DNA
<213> ORGANISM: Nitrospira moscoviensis

<400> SEQUENCE: 49
agcctggcag taccctct        18

<210> SEQ ID NO 50
<211> LENGTH: 18
<212> TYPE: DNA
<213> ORGANISM: Artificial Sequence
<220> FEATURE:
<223> OTHER INFORMATION: Consensus sequence of 16s rDNA sequences of
      nitrite oxidisers from various bacterial phyla

<400> SEQUENCE: 50
cctgtgctcc atgctccg        18

<210> SEQ ID NO 51
<211> LENGTH: 18
<212> TYPE: DNA
<213> ORGANISM: Nitrobacter hamburgensis

<400> SEQUENCE: 51
cctgtgctcc atgctccg        18

<210> SEQ ID NO 52
<211> LENGTH: 18
<212> TYPE: DNA
<213> ORGANISM: Nitrospina gracilis

<400> SEQUENCE: 52
cctgtgctcc atgctccg        18

<210> SEQ ID NO 53
<211> LENGTH: 18
<212> TYPE: DNA
<213> ORGANISM: Nitrococcus mobilis

<400> SEQUENCE: 53
cctgtcatcc ggttcccg                                               18

<210> SEQ ID NO 54
<211> LENGTH: 18
<212> TYPE: DNA
<213> ORGANISM: Nitrospira moscoviensis

<400> SEQUENCE: 54
cctgagcacg ctggtatt                                               18

<210> SEQ ID NO 55
<211> LENGTH: 18
<212> TYPE: DNA
<213> ORGANISM: Nitrospina marina

<400> SEQUENCE: 55
cctgagctcg ctccccctt                                              18

<210> SEQ ID NO 56
<211> LENGTH: 18
<212> TYPE: DNA
<213> ORGANISM: Magnetobacterium bavaricum

<400> SEQUENCE: 56
cctgtgcaag ctctccct                                               18

<210> SEQ ID NO 57
<211> LENGTH: 18
<212> TYPE: DNA
<213> ORGANISM: Nitrospira

<400> SEQUENCE: 57
cctgagcagg atggtatt                                               18

<210> SEQ ID NO 58
<211> LENGTH: 18
<212> TYPE: DNA
<213> ORGANISM: Nitrospira

<400> SEQUENCE: 58
cctgagcacg ctggtatt                                               18

<210> SEQ ID NO 59
<211> LENGTH: 18
<212> TYPE: DNA
<213> ORGANISM: Nitrospira

<400> SEQUENCE: 59
cctgagcagg atggtgtt                                               18

<210> SEQ ID NO 60
<211> LENGTH: 16
<212> TYPE: DNA
<213> ORGANISM: Artificial Sequence
<220> FEATURE:
<223> OTHER INFORMATION: E. coli 16S rDNA primer 530f.

<400> SEQUENCE: 60

```
gtgccagcmg ccgcgg                                                           16

<210> SEQ ID NO 61
<211> LENGTH: 22
<212> TYPE: DNA
<213> ORGANISM: Artificial Sequence
<220> FEATURE:
<223> OTHER INFORMATION: E. coli 16S rDNA primer 1492f.

<400> SEQUENCE: 61
tacggytacc ttgttacgac tt                                                    22

<210> SEQ ID NO 62
<211> LENGTH: 20
<212> TYPE: DNA
<213> ORGANISM: Artificial Sequence
<220> FEATURE:
<223> OTHER INFORMATION: E. coli 16S rDNA primer 27f.

<400> SEQUENCE: 62
agagtttgat cctggctcag                                                       20
```

METHOD FOR THE DETECTION OF AQUATIC NITRITE OXIDIZING MICROORGANISMS OF THE GENUS NITROSPIRA

TECHNICAL FIELD

This invention relates to the removal of nitrogenous compounds from wastewater. In particular, the invention relates to an isolated consortium of microorganisms capable of nitrification of wastewater. The invention also relates to methods of identifying microorganisms capable of nitrification of wastewater and oligonucleotide primers and DNA probes suitable for use in the methods.

INTRODUCTION

The removal of nitrogenous compounds from sewage effluents is an important aspect in the remediation of wastewaters. The presence of ammonia, nitrite and nitrate in wastewater discharges can cause numerous problems ranging from eutrophication (Meganck and Faup, 1988) of the receiving aquatic environment to aspects of public health concern such as nitrate contamination of drinking water. Nitrogen is biologically removed from wastewaters in a two step process of nitrification (ammonia oxidised to nitrate) (Randall, 1992; Robertson and Kuenen, 1991) and denitrification (nitrate reduced to dinitrogen gas that dissipates into the atmosphere) (Blackburn, 1983; Robertson and Kuenen, 1991). Nitrification is the first and most sensitive step of the process and can be further subdivided into two steps: ammonia oxidation to nitrite and nitrite oxidation to nitrate. The two steps are carried out by separate bacterial groups and for both groups, the total diversity of organisms with this phenotype is small.

Therefore, nitrification is a process where reduced nitrogen compounds, generally ammonium ($NH_4^+$), are microbiologically oxidised to nitrate ($NO_3^-$) via nitrite ($NO_2^-$) under aerobic conditions (Halling-Sørensen and Jørgensen, 1993). The overall reactions and possible organisms responsible are:

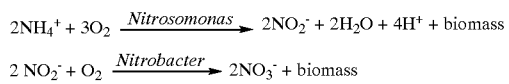

$$2NH_4^+ + 3O_2 \xrightarrow{Nitrosomonas} 2NO_2^- + 2H_2O + 4H^+ + biomass$$

$$2 NO_2^- + O_2 \xrightarrow{Nitrobacter} 2NO_3^- + biomass$$

The Gram negative chemoautotrophic nitrite oxidising bacteria are physiologically distinct, as they all possess the ability to use nitrite as their energy source and to assimilate $CO_2$, via the Calvin Benson cycle, as a carbon source for cell growth (Bock et al., 1992). For each molecule of $CO_2$ fixed, 100 molecules of nitrite need to be oxidized, emphasising the high energy demands placed on these cells. The overall stoichiometry of nitrite oxidation is (Halling-Sørensen and Jørgensen, 1993):

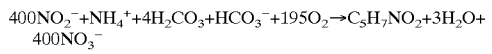

$$400NO_2^- + NH_4^+ + 4H_2CO_3 + HCO_3^- + 195O_2 \rightarrow C_5H_7NO_2 + 3H_2O + 400NO_3^-$$

These bacteria can typically also use nitric oxide (NO) instead of $NO_2^-$ as an electron source (Bock et al., 1992). Not all of the known nitrifying bacteria are obligate chemoautotrophs. In fact, many strains of Nitrobacter can grow well as heterotrophs, where both energy and carbon are obtained from organic carbon sources, or mixotrophically (a combination of both autotrophic and heterotrophic behaviour). These bacteria are collectively known as facultative chemoautotrophs. Therefore, bacterial strains can grow three ways; aerobically and autotrophically, aerobically and mixotrophically or anaerobically and heterotrophically. In mixotrophic growth, $NO_2^-$ is oxidized in preference to organic carbon substrates like acetate, pyruvate and glycerol. Both autotrophic and heterotrophic growth is usually slow and inefficient.

As a generalisation, most strains of Nitrobacter seem to be able to grow faster as mixotrophs than as heterotrophs and faster heterotrophically or chemo-heterotrophically than chemoautotrophically.

Four genera are currently recognised: Nitrobacter, Nitrospina, Nitrococcus and Nitrospira (Halling-Sørensen and Jørgensen, 1993). Nitrospina and Nitrococcus are unable to grow heterotrophically or mixotrophically (Bock et al., 1992). One species of Nitrospira, *Nitrospira marina*, can grow autotrophically and mixotrophically, (Bock et al., 1992) whereas *Nitrospira moscoviensis* is an obligate autotroph (Ehrich, et al., 1995). These nitrite oxidizers have also been conventionally classified based on phenotypic characters like their cell shape and the ultrastructure of their intracytoplasmic membranes. Doubling times of Nitrobacter can range from 12 to 59 hours, or even as long as 140 hours (Halling-Sørensen and Jørgensen, 1993). These are therefore very slow growing bacteria.

In wastewater treatment systems, Nitrosomonas (an ammonia oxidizer) and Nitrobacter (a nitrite oxidizer) are the two autotrophs presumed to be responsible for nitrification because they are the commonest ammonia and nitrite oxidizers isolated from these environments (Halling-Sørensen and Jørgensen, 1993). Although ammonia oxidizers have been intensively studied by the use of molecular methods (Wagner et al., 1995; Wagner et al., 1996), the nitrite oxidizers have not been similarly investigated. Since the microorganisms responsible for nitrite oxidation in wastewater treatment plants were presumed to be from the genus Nitrobacter, mathematical modeling of the process has used data relevant to this genus. However, fluorescent in situ hybridization (FISH) probing of activated sludge mixed liquors with Nitrobacter specific probes (Wagner et al., 1996) could not confirm the presence of these organisms suggesting that they were not responsible for this major component of nitrogen remediation. Indeed, Nitrobacter could not be found in other aquatic environments (Hovanec and DeLong, 1996) when specific FISH probes were employed. It was speculated that other bacteria were likely responsible for nitrite oxidation (Hovanec and DeLong, 1996; Wagner et al., 1996).

Knowledge of the microorganisms responsible for nitrification of wastewater is desirable for the efficient management of treatment systems. It would also be advantageous to have available biomass which can be added to a system to implement or improve nitrification. However, as indicated above, there is no certainty in the art as to the actual microorganisms responsible for nitrification nor are there methods available for identifying such organisms.

SUMMARY OF THE INVENTION

It is an object of the invention to provide a consortium of microorganisms that can be used for nitrification of wastewater.

A further object of the invention is to provide a method of identifying microorganisms capable of nitrification of wastewater.

According to a first embodiment of the invention, there is provided a consortium of microorganisms capable of nitrite oxidation in wastewater, which consortium is enriched in members of the Nitrospira phylum.

According to a second embodiment of the invention, there is provided an oligonucleotide primer for PCR amplification of Nitrospira DNA, said primer comprising at least 12 nucleotides having a sequence selected from:
(i) any one of SEQ ID NO: 1 to SEQ ID NO: 13; or
(ii) a DNA sequence having at least 92% identity with any one of SEQ ID NO: 1 to SEQ ID NO: 13.

According to a third embodiment of the invention, there is provided a primer pair for PCR amplification of Nitrospira DNA, said primer pair comprising:
(a) a first oligonucleotide of at least 12 nucleotides having a sequence selected from one strand of a bacterial 16S rDNA gene; and
(b) a second oligonucleotide of at least 12 nucleotides having a sequence selected from the other strand of said 16S rDNA gene downstream of said first oligonucleotide sequence; wherein at least one of said first and second oligonucleotides is selected from:
(i) any one of SEQ ID NO: 1 to SEQ ID NO: 13; or
(ii) a DNA sequence having at least 92% identity with any one SEQ ID NO: 1 to SEQ ID NO: 13.

According to a fourth embodiment of the invention, there is provided a probe for detecting Nitrospira DNA, said probe comprising at least 12 nucleotides having a sequence selected from:
(i) any one of SEQ ID NO: 1 to SEQ ID NO: 13; or
(ii) a DNA sequence having at least 92% identity with any one of SEQ ID NO: 1 to SEQ ID NO: 13.

According to a fifth embodiment of the invention, there is provided a kit comprising:
at least one primer according to the second embodiment;
at least one primer pair according to the third embodiment; or
at least one probe according to the fourth embodiment.

According to a sixth embodiment of the invention, there is provided a method of detecting a Nitrospira species in a sample, said method comprising the steps of:
(a) lysing cells in said sample to release genomic DNA;
(b) contacting denatured genomic DNA from step (a) with a primer pair according to the third embodiment;
(c) amplifying Nitrospira DNA by cyclically reacting said primer pair with said DNA to produce an amplification product; and
(d) detecting said amplification product.

According to a seventh embodiment of the invention, there is provided a method of quantitating the level of a Nitrospira species in a sample, said method comprising the steps of:
(a) lysing cells in said sample to release genomic DNA;
(b) contacting denatured genomic DNA from step (a) with a primer pair according to the third embodiment;
(c) amplifying Nitrospira DNA by cyclically reacting said primer pair with said DNA to produce an amplification product; and
(d) detecting said amplification product and quantitating the level of said product by comparison with at least one reference standard.

According to an eighth embodiment of the invention, there is provided a method of detecting a Nitrospira species in a sample, said method comprising the steps of:
(a) lysing cells in said sample to release genomic DNA;
(b) contacting denatured genomic DNA from step (a) with a labeled probe according to the fourth embodiment under conditions which allow hybridisation of said genomic DNA said probe;
(c) separating hybridised labeled probe and genomic DNA from unhybridised labeled probe; and
(d) detecting said labeled probe-genomic DNA hybrid.

According to a ninth embodiment of the invention, there is provided a method of detecting cells of a Nitrospira species in a sample, said method comprising the steps of:
(a) treating cells in said sample to fix cellular contents;
(b) contacting said fixed cells from step (a) with a labeled probe according to the fourth embodiment under conditions which allow said probe to hybridise with RNA within said fixed cell;
(c) removing unhybridised probe from said fixed cells; and
(d) detecting said labeled probe-RNA hybrid.

BRIEF DESCRIPTION OF THE DRAWINGS

FIG. 8 is an alignment of sequences of 16S rDNA from Nitrospira clones identified in a nitrite-oxidising SBR and from other sources. The sequence identifiers for the sequences presented in the figure are as follows: SBR1024 (SEQ ID NO:1), SBR1015 (SEQ ID NO:2), GC86 (SEQ ID NO:3, SBR2046 (SEQ ID NO:4), RC25 (SEQ ID NO:5), RC19, (SEQ ID NO:6), SBR2016 (SEQ ID NO:7), RC7 (SEQ ID NO:8), RC14 (SEQ ID NO:9), RC99 (SEQ ID NO:10), RC11 (SEQ ID NO:11), RC73 (SEQ ID NO:12), and RC90 (SEQ ID NO:13).

BEST MODE AND OTHER MODES OF CARRYING OUT THE INVENTION

Figure 1:
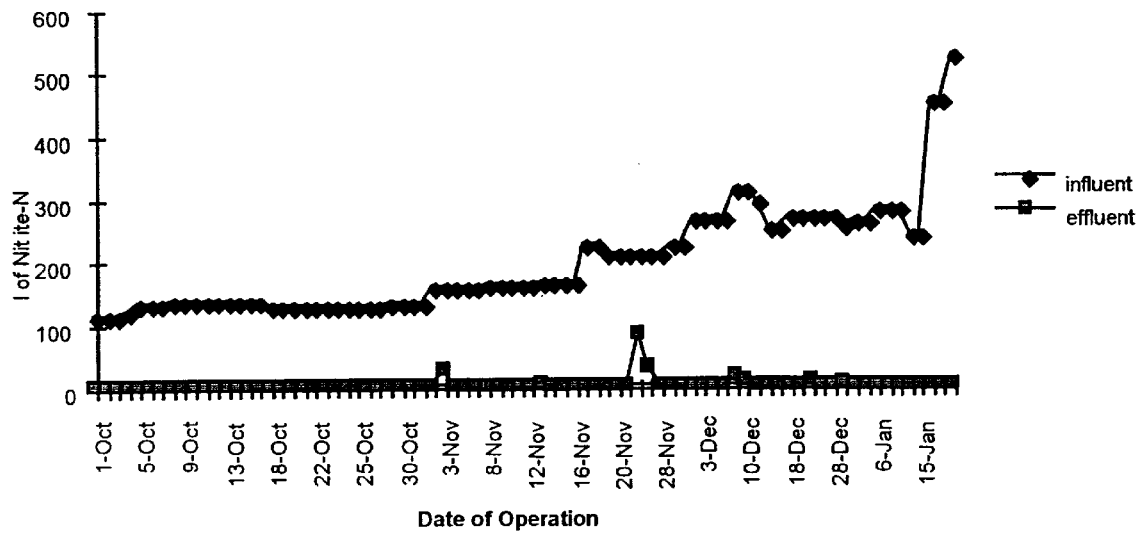
FIG. 1 is a graph showing influent and effluent $NO_2$—N concentrations for an automated laboratory-scale reactor operating as a sequencing batch reactor at 2 cycles/day with strong selection for nitrite oxidising biomass (NOSBR).

The following abbreviations are used hereafter:

| | |
|---|---|
| SBR | sequencing batch reactor |
| NOSBR | nitrite oxidising SBR |
| NOM | nitrite oxidising medium |
| HRT | hydraulic retention time |
| MLSS | mixed liquor suspended solids |
| BNR | biological nutrient removal |
| DO | dissolved oxygen |
| PCR | polymerase chain reaction |
| REA | restriction enzyme analysis |
| OTU | operational taxonomic unit |
| bp(s) | base pair(s) |

The one-letter code for nucleotides in DNA conforms to the IUPAC-IUB standard described in *Biochemical Journal* 219, 345–373 (1984).

The term "comprise", or variations of the term such as "comprises" or "comprising", are used herein to denote the inclusion of a stated integer or stated integers but not to exclude any other integer or any other integers, unless in the context or usage an exclusive interpretation of the terms is required.

The present inventors have developed a specific nitrifying biomass that is largely comprised of bacteria that are most closely related to *Nitrospira moscoviensis*. It is believed that a range of species of Nitrospira are involved in the process. The inventors have shown that these bacteria are likely to be more dominant in reactors with good nitrification performance than bacteria from the genus Nitrobacter. A range of studies have failed to find Nitrobacter in nitrifying processes (Hovanec & DeLong, 1996; Wagner et al., 1996) and evidence is provided below that the organisms responsible for this important biochemical reaction in wastewater treatment processes (both suspended and attached growth processes) are from the Nitrospira phylum in the domain Bacteria.

With reference to the first embodiment of the invention, the nitrifying biomass can be produced by presenting a feed comprising nitrite, dissolved oxygen and dissolved carbon dioxide but which is free of organic carbon to seed sludge from any sewage plant exhibiting nitrification. The seed sludge is advantageously from a domestic wastewater treatment plant but can also be from an abattoir wastewater treatment plant. The nitrite component of the feed can be as low as about 400 mg/L nitrite-N. The oxygen and carbon dioxide can conveniently be provided as air bubbled through the solution.

Turning to the second embodiment of the invention, oligonucleotide primers typically have a length of about 12 to 50 nucleotides. A preferred length is 12 to 22 nucleotides. Particularly preferred primers are the following:

| | |
|---|---|
| 5' CGGGAGGGAAGATGGAGC 3' | (SEQ ID NO: 14) |
| 5' CCAACCCGGAAAGCGCAGAG 3' | (SEQ ID NO: 15) |
| 5' AGCCTGGCAGTACCCTCT 3' | (SEQ ID NO: 16) |

Oligonucleotide primer pairs according to the third embodiment of the invention comprise an oligonucleotide primer that will anneal to one strand of the target sequence and a second oligonucleotide primer which will anneal to the other, complementary, strand of the target sequence. It will be appreciated that the second oligonucleotide primer must anneal to the complementary strand downstream of the first oligonucleotide primer sequence, which occurs in the complementary strand, to yield a double stranded amplification product in the PCR. The amplification product is of a size that facilitates detection. Typically, the first and second oligonucleotide primer sites in the target DNA are separated by 50 to 1,400 bps. A preferred separation is 400 to 1,000 bps.

The probes of the fourth embodiment, as indicated above, can have a size as small as 12 nucleotides. Typically, however, probes have a length of 15 to 50 nucleotides. A preferred probe length is 15 to 22 nucleotides, particularly for in situ hybridisation according to the method of the ninth embodiment.

The oligonucleotide primers included in kits according to the fifth embodiment of the invention can be individual oligonucleotide primers appropriate for the detection of Nitrospira or a primer pair. Oligonucleotide primer pairs are advantageously provided as compositions. Additional oligonucleotide primers can also be included in kits for use in control reactions. For detection purposes, DNA probes can also be included in kits.

Kits according to the fifth embodiment of the invention can further comprise reagents used in PCR and hybridisation reactions. Such reagents include buffers, salts, detergents, nucleotides and thermostable polymerase. Such reagents are advantageously provided as solutions to facilitate execution of PCR or hybridisation. Solutions can be compositions comprising a number of reagents as is well known in the art.

The general techniques used in the methods of the sixth to ninth embodiments, and factors to be considered in selecting PCR primers and probes, will be known to those of skill in the art. Such techniques are described, for example, in Sambrook et al. (1989) and Stackebrandt and Goodfellow (1991), the entire contents of which are incorporated herein by cross reference. Particularly relevant chapters in Stackebrandt and Goodfellow are Chapter 7, "The Polymerase Chain Reaction" by S. Giovannoni, and Chapter 8, "Development and Application of Nucleic Acid Probes" by D. A. Stohl and R. Amann.

Non-limiting examples of the invention will now be provided.

General Methods

The total community DNAs from the NOSBR sludge (RC) and the seed sludge (GC) were isolated, the 16S rDNAs were polymerase chain reaction (PCR) amplified and cloned using previously published methods (Blackall, 1994; Blackall et al., 1994; Bond et al., 1995). Inserts from 102 clones in the RC library were amplified and grouped by HaeIII restriction enzyme digestion banding profiles (REA) into operational taxonomic units (OTUs) (Weidner et al., 1996). Clone inserts from representatives of RC OTUs and all 77 clones from the GC library were PCR amplified and partially sequenced (Blackall, 1994) using 530f GTGC-CAGCMGCCGCGG (SEQ ID NO:60) (Lane, 1991) primer. Inserts from a selection of clones were fully sequenced (Blackall, 1994). Sequence data were analysed according to previously published methods (Blackall et al., 1994) which included BLAST (Altschul et al., 1990) comparisons and phylogenetic analyses (Felsenstein, 1993).

EXAMPLE 1

Selection of a Nitrifying Biomass

In this example, we describe the use of a laboratory-scale reactor as a sequencing batch reactor (SBR) with strong selection for a nitrite oxidising biomass. Seed sludge was from the Merrimac domestic wastewater treatment plant operated by the Gold Coast City Council and located at Merrimac, Queensland 4226, Australia. The reactor set-up will be hereafter referred to as the "Nitrite Oxidising SBR", or "NOSBR".

Reactor. A laboratory chemostat with a working volume of 1 L was operated in the dark at 24° C. as the NOSBR. The influent nitrite oxidising medium (NOM) was a synthetic waste water mix comprising per L: 400 to 3,200 mg $KNO_2$, 3.75 g $MgSO_4.7H_2O$, 250 mg $CaCl_2.2H_2O$, 10 g $KH_2PO_4$, 10 g $K_2HPO_4$, 200 mg $FeSO_4.7H_2O$, and 20 g $NaHCO_3$. The pH of the medium was adjusted to 7.0, but the reactor was not equipped with pH control. Dissolved oxygen was maintained at 1.6–2.0 mg/L and $CO_2$ was introduced by bubbling air through the liquid in the NOSBR. Surface biomass growth was precluded by regular scrubbing of all solid surfaces with a brush. Four cycles per day giving a hydraulic retention time (HRT) of 12 hr were performed with the following sequences:

1) Feed of 500 ml of fresh medium—30 min (0 to 0.5 hr)
2) React (aeration)—4.5 hr (0.5 to 5 hr)
3) Settle—40 min (5 to 5.7 hr)
4) Decant 500 ml of supernatant—20 min (5.7 to 6 hr)
5) Total time per cycle—6 hr.

Automatic timers controlled the magnetic stirrer (100 rpm), peristaltic pumps (feed and decant), and air pump for the cycles. Sludge biomass was not wasted from the reactor, but periodically, biomass was collected for testing which facilitated maintenance of a relatively steady amount of biomass in the SBR.

At start up, 1 L of mixed liquor suspended solids (MLSS) from a full scale Biological Nutrient Removal (BNR, nitrogen and phosphorus removal) plant was added to the NOSBR which was operated manually with the NOM. Initial manual and then automatic operation with 2-cycles per day (feed—[500 ml] 40 min; react—10 hr; settle—40 min; and decant [500 ml]—40 min) occurred for some months before initiation of the 4-cycles per day scheme (see above).

Monitoring. Chemical analyses of feed, mixed liquor and effluent were regularly done for nitrite-N ($NO_2$—N), nitrate-N ($NO_3$—N), and ammonium-N ($NH_4^+$—N) using spectrometric assays (Merck, Melbourne, Australia). To preclude the removal of excessive biomass, these analyses were done with 2 ml samples. The MLSS of the NOSBR was determined in duplicate 10 ml samples of mixed liquor. These were filtered onto pre-dried Whatman GF/C filters, and then dried to a constant weight at 105 degree C. A pH meter was used to periodically monitor pH in the mixed liquor and effluent. A portable dissolved oxygen (DO) meter and probe were used to periodically monitor the DO in the NOSBR.

Figure 2:
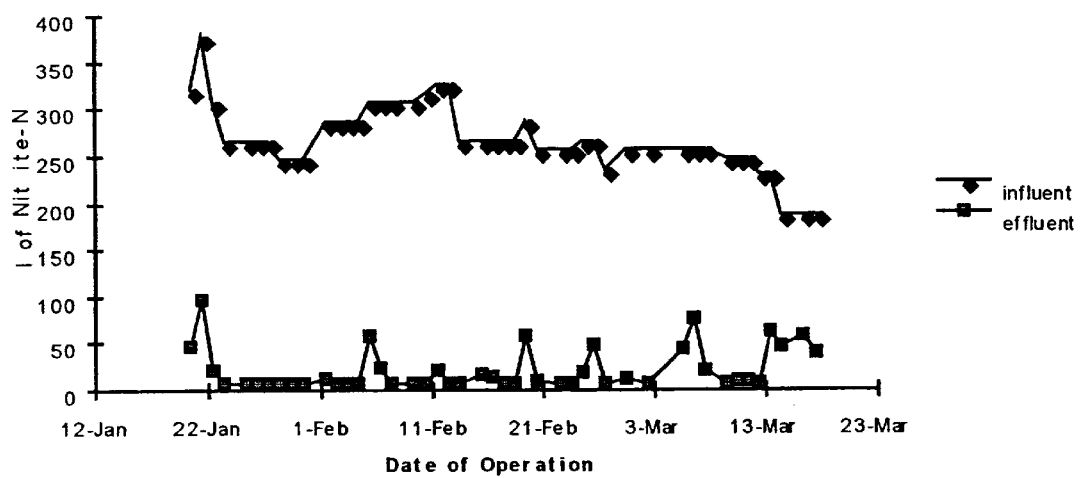
FIG. 2 is a graph showing influent and effluent $NO_2$—N concentrations of the NOSBR operating at 4 cycles/day.

Results of operation. Varying influent nitrite levels were employed to study a range of features of the selected nitrite oxidising biomass. The operating data for the influent and effluent nitrite levels of the NOSBR during the automated 2 cycles/day period are presented in FIG. 1 and for the automated 4 cycles/day in FIG. 2. The data presented in these figures show that the microbial community are able to remove all the nitrite from the influent in a matter of hours.

Attributes of the NOSBR Mixed Liquor

Figure 3:
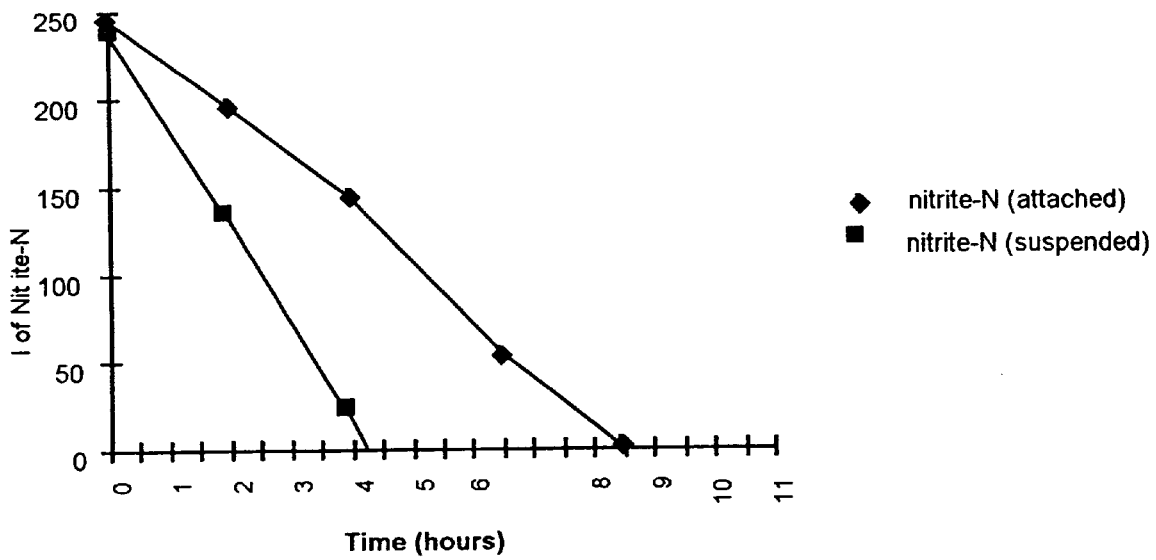
FIG. 3 is a graph of mixed liquor nitrite-N concentrations during the react period of the NOSBR cycle for attached growth and for suspended growth.

1. Suspended versus attached growth—2 cycles/day. To generate attached growth, the regular scrubbing regime of the reactor was suspended for two weeks. The vast bulk of the biomass was then attached to surfaces in the reactor. The little remaining suspended biomass was discharged from the reactor which was then filled with 1 L of half strength NOM. Regular sampling and nitrite analyses were done during the react period of one cycle with all the biomass attached to the reactor surfaces. The results of this experiment are presented in FIG. 3. The results show that suspended biomass has twice the nitrite oxidation rate than the attached biomass but both systems are effective in removing nitrite from the influent.

Following the experiment described in the previous paragraph, the biomass was completely scrubbed from the surfaces to the liquid. The reactor was operated for two cycles with biomass scrubbing. A similar one-cycle study was performed as with the attached growth but with all biomass suspended. The biofilm growth exhibited a nitrite oxidation rate of 29 mg $NO_2$—N/hr and the suspended growth form showed a rate of 58 mg $NO_2$—N/hr. It was assumed that the biomass concentration was the same for both studies since none had been removed between them.

2. pH correlation with nitrification. It was observed that when the pH of the effluent fell below 7.4, nitrite-N was present in the effluent. If the pH rose above 7.4 for short periods, no effect to nitrification was observed. Therefore, pH values below 7.4 were detrimental to nitrification.

Figure 4:
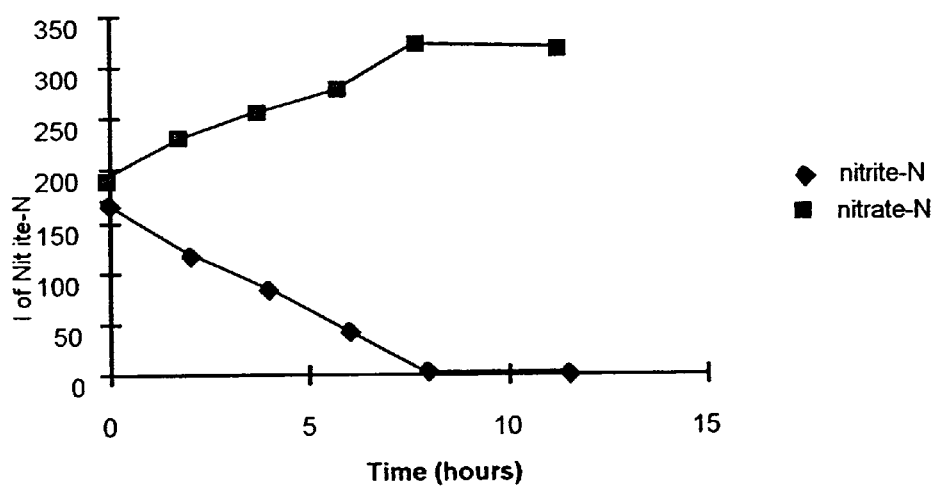
FIG. 4 is a graph showing nitrite-N and nitrate-N concentrations in the mixed liquor during the react period of the NOSBR.

3. Cyclic studies. FIG. 4 shows the results for periodic measurements of nitrite-N and nitrate-N during the react period of the reactor during 2 cycles/day The results presented in these figures show that the bacterial population in the reactor oxidised nitrite to nitrate in a stoichiometric manner with 160 mg/l of nitrite-N being oxidised to 160 mg/l of nitrate-N (170 mg/l at the start of the react period and 330 mg/l when the nitrite-N was exhausted). The rate of nitrite oxidation and nitrate production also appeared to be linear, showing that the oxidation process was not limited by any external factors.

Figure 5:
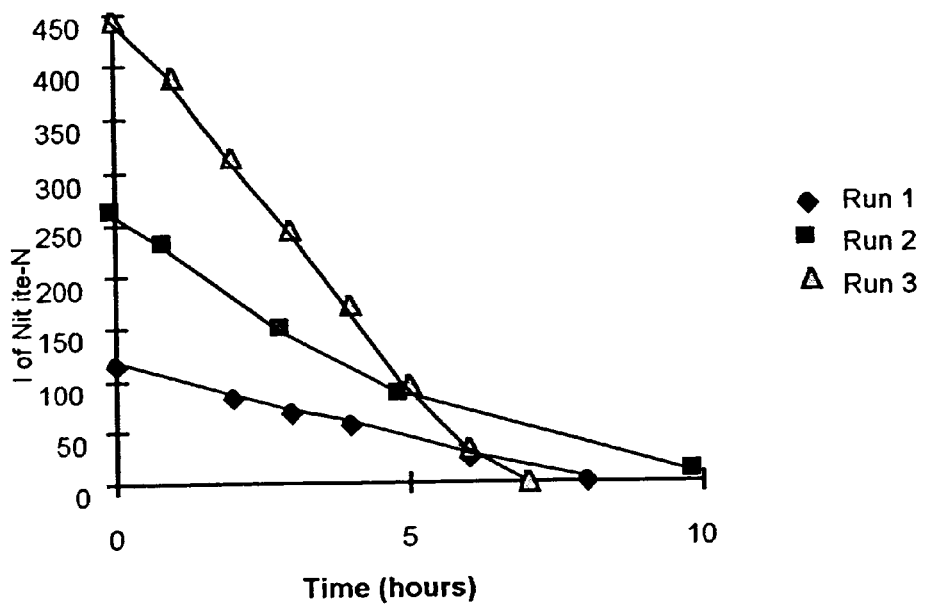
FIG. 5 ia a graph showing mixed liquor nitrite-N concentrations during the react period in three stages of the NOSBR operated at 2 cycles/day with different concentrations of nitrite in the feed.
Figure 6:
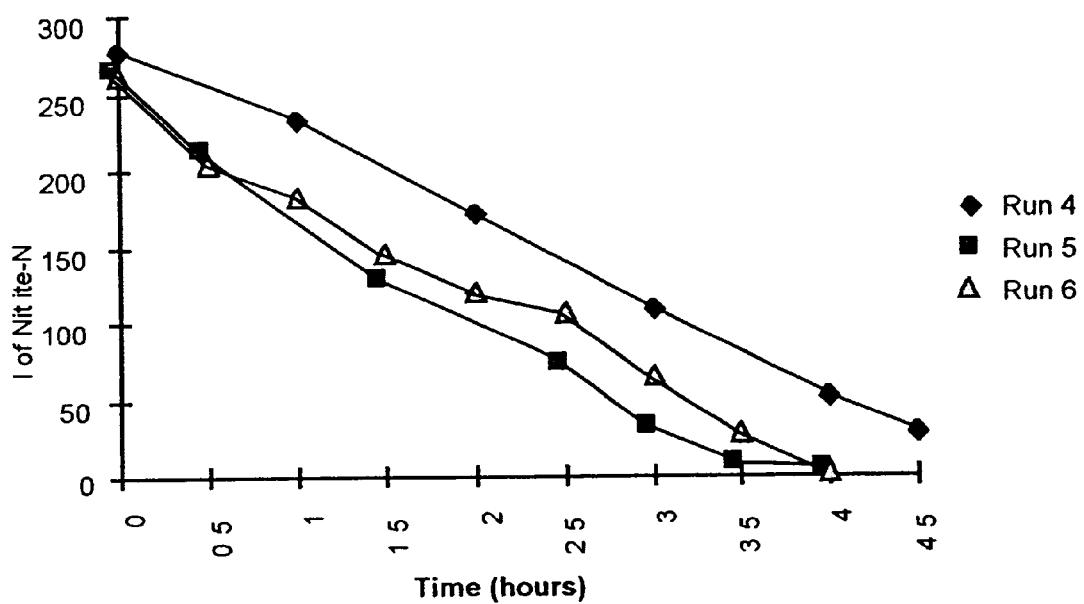
FIG. 6 is a graph of mixed liquor nitrite-N concentrations during the react period in three representative cycles during operation of the NOSBR at 4 cycles/day.

Studies measuring nitrite reaction in the reactor are shown for both 2 cycles/day (FIG. 5) and 4 cycles/day operation (FIG. 6). The significance of these results is that the biomass is robust in its capacity to oxidise nitrite under a range of operating conditions.

EXAMPLE 2

The Microbiology of the NOSBR

In this example, we describe the microbiological characterisation of the nitrifying microorganisms present in the biomass selected in the NOSBR described in Example 1. Methods used in the characterisation have been described by Blackall (1994) and Bond et al. (1995), the entire contents of which disclosures are incorporated herein by cross-reference.

Total microbial community DNA from both the seed BNR sludge (GC) and from the reactor after six months of operation (RC) was obtained. The 16S rDNA from each DNA extract were separately amplified by polymerase chain reaction (PCR), and then for each, clone libraries were prepared (Blackall, 1994; Bond et al., 1995).

Inserts from a total of 77 clones from the GC clone library were partially sequenced with the primer 530f and phylogenetically analysed (Blackall et al., 1994) (Table 1). The majority of the clone sequences grouped with the proteobacterial phylum, while 4% (3 clones; GC3, GC86 and GC109) grouped with the phylum Nitrospira.

TABLE 1

Phyla from the Domain Bacteria Represented in the GC Clone Library

| Phylum in Domain Bacteria | Percentage in clone library |
| --- | --- |
| Proteobacteria | |
| Alpha | 5 |
| Beta | 29 |
| gamma | 18 |
| delta | 4 |
| High mol % G + C Gram positives | 10 |
| Low mol % G + C Gram positives | 7 |
| Flexibacter/Cytophaga/Bacteroides | 5 |
| Nitrospira | 4 |
| Planctomycetales | 9 |
| Unaffiliated | 9 |

Restriction Enzyme Analysis (REA) of the RC library was done to group clones into operational taxonomic units (OTUs) in advance of partial or complete clone insert sequencing (Weidner et al., 1996). Thirteen different OTUs were found when HaeIII was employed as the restriction enzyme to digest the inserts from 102 clones. The large majority of the clone inserts (88% or 90 clones) were found in one OTU while the remaining 12% (12 clones) comprised individuals in 12 other OTUs. Each of the clone inserts from the latter 12 OTUs and six of the large former group (RC7, RC11, RC16, RC25, RC73, and RC99) were partially sequenced and phylogenetically analysed. These six and one of the other OTUs (RC90) were found to have partial insert sequences that phylogenetically grouped with the Nitrospira phylum. From this analysis, it was concluded that 91 clones or 89% of the clone library originated from bacteria in the Nitrospira phylum. In the phylogenetic analysis, one of the other OTUs (RC44) grouped with Nitrobacter. It was concluded that the organisms responsible for nitrification in the NOSBR were likely to be from the Nitrospira phylum.

Near complete insert sequence analyses were done for the following clones:

six RC clones of the original partial sequences—RC7, RC11, RC25, RC73, RC90, and RC99 (RC16 omitted);

two RC clones from the Nitrospira OTU (RC14 and RC19);

one of the three GC Nitrospira clones (GC86); and four clones from a clone library prepared by Bond et al. (1995) that phylogenetically grouped in the Nitrospira phylum.

Figure 7:
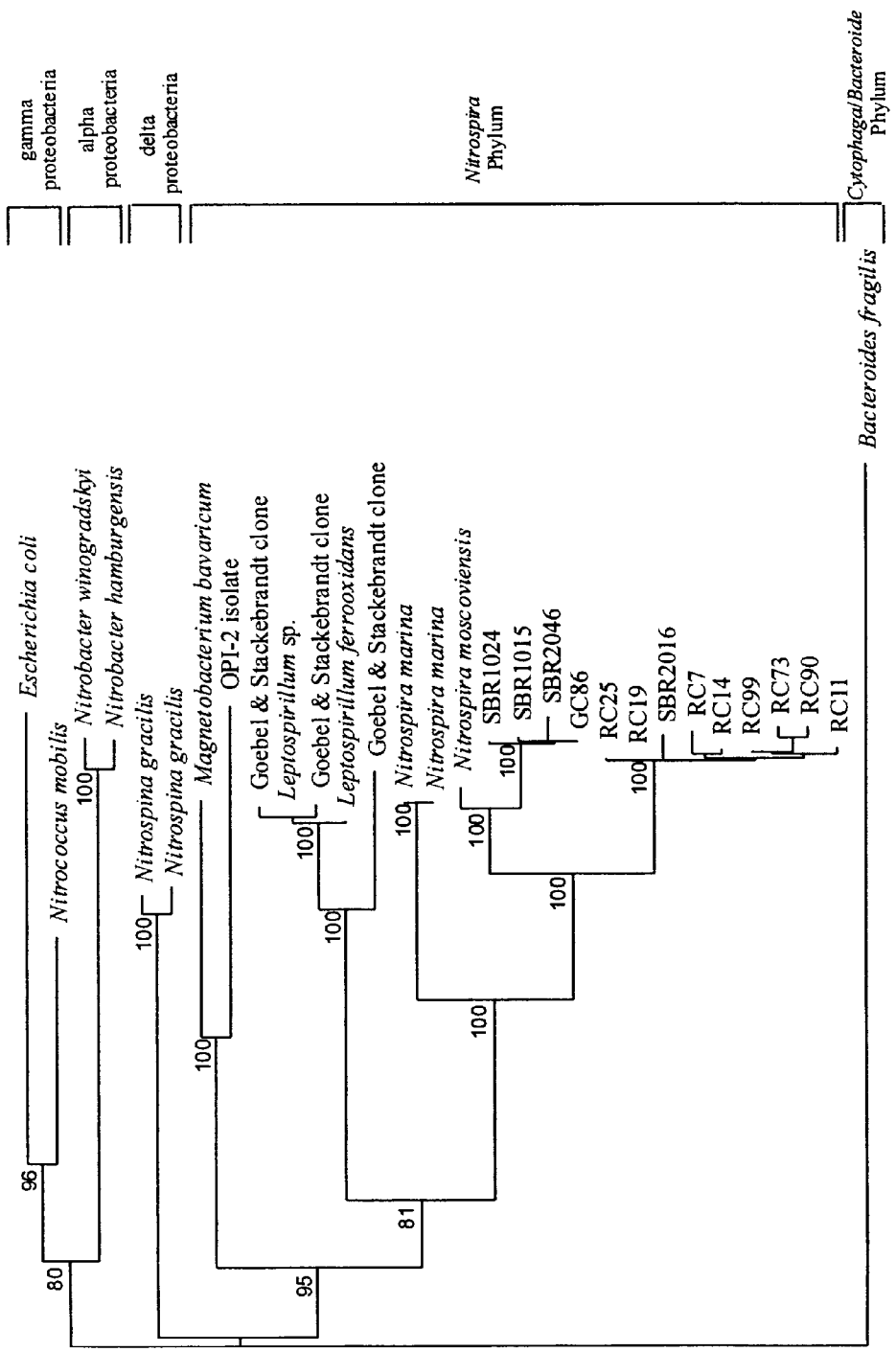
FIG. 7 is an evolutionary distance tree derived from a comparison of 16S rDNA sequences from nitrite oxidising bacteria and clone sequences from three different 16S rDNA clone libraries (RC, GC, and SBR).

The data were phylogenetically analysed as shown in FIG. 7. The two clone clades would likely comprise two separate species with the RC clones possibly comprising more than one species.

Sequences of clones from the two Nitrospira clades were subjected to direct pairwise sequence comparison. The results of this comparison are presented in Table 2. The table is a similarity matrix showing the percent similarity between 16S rDNA sequences of *Nitrospira moscoviensis, Nitrospira marina* and 13 near complete sequences from clone inserts from a full scale biological nutrient removal activated sludge plant (GC86), from the NOSBR (RC clone numbers) and from clones for which the partial sequences had been previously reported (SBR clones; Bond et al., 1995). The similarity matrix showed that the first clade (SBR1015, SBR1024, SBR2046, GC86) had an average 16S rDNA comparison value of 99.4% while for the second clade (RC7, RC11, RC14, RC19, RC25, RC73, RC90, RC99, SBR2016), this value was 98.7%. The highest comparative value between an RC clone sequence and *N. moscoviensis* was 93.4% for RC25. From the sequence data analysis, the two clone clades would likely comprise two separate species, with the RC clones possibly comprising more than one species.

Sequence data for the SBR, GC and RC clones are presented in FIG. 8. In this figure, sequences are divided into blocks with numbers given in square brackets above each block. The clone identification is given at the left of a line of sequence in each block. Dashes represent unknown nucleotides while full stops represent alignment breaks.

The sequences of clones are also presented as sequence listings as follows:

| Clone | Sequence Listing Number |
| --- | --- |
| SBR1024 | 1 |
| SBR1015 | 2 |
| GC86 | 3 |
| SBR2046 | 4 |
| RC25 | 5 |
| RC19 | 6 |
| SBR2016 | 7 |
| RC7 | 8 |
| RC14 | 9 |
| RC99 | 10 |
| RC11 | 11 |
| RC73 | 12 |
| RC90 | 13 |

TABLE 2

| Species or clone | Percent sequence similarity with species of strain number | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| 1. Nitrospira moscoviensis | | | | | | | | | | | | | | | |
| 2. SBR1024 | 96.3 | | | | | | | | | | | | | | |
| 3. SBR1015 | 96.1 | 99.6 | | | | | | | | | | | | | |
| 4. GC86 | 96.1 | 99.6 | 99.4 | | | | | | | | | | | | |
| 5. SB2046 | 95.8 | 99.3 | 99.4 | 99.2 | | | | | | | | | | | |
| 6. RC25 | 93.4 | 93.4 | 93.6 | 93.6 | 93.1 | | | | | | | | | | |
| 7. RC19 | 93.2 | 93.1 | 93.0 | 93.2 | 92.7 | 98.8 | | | | | | | | | |
| 8. SB2016 | 93.0 | 92.7 | 92.8 | 92.6 | 92.4 | 99.1 | 98.7 | | | | | | | | |
| 9. RC7 | 92.9 | 93.1 | 93.2 | 92.9 | 92.8 | 98.7 | 98.7 | 98.5 | | | | | | | |
| 10 RC14 | 92.8 | 93.0 | 93.1 | 93.1 | 92.7 | 98.7 | 98.9 | 98.5 | 99.3 | | | | | | |
| 11 RC99 | 92.7 | 92.9 | 93.0 | 93.0 | 92.6 | 98.5 | 98.7 | 98.4 | 99.2 | 99.6 | | | | | |
| 12 RC11 | 92.6 | 92.8 | 93.0 | 92.9 | 92.5 | 98.5 | 98.7 | 98.4 | 99.0 | 99.5 | 99.7 | | | | |
| 13 RC73 | 92.2 | 92.5 | 92.6 | 92.6 | 92.1 | 98.0 | 98.2 | 97.9 | 98.7 | 99.1 | 99.4 | 99.4 | | | |
| 14 RC90 | 92.1 | 92.1 | 92.3 | 92.2 | 91.8 | 98.1 | 98.6 | 98.0 | 98.1 | 98.6 | 98.8 | 98.8 | 99.0 | | |
| 15 Nitrospira marina | 88.7 | 88.2 | 88.3 | 88.3 | 87.8 | 88.1 | 87.6 | 87.2 | 87.2 | 87.1 | 87.1 | 87.1 | 86.5 | 86.6 | |
| 16 Nitrospira marina | 88.0 | 88.0 | 88.2 | 88.1 | 87.7 | 87.9 | 87.5 | 87.2 | 87.2 | 87.1 | 87.1 | 87.1 | 86.5 | 86.6 | 99.9 |

EXAMPLE 3

Identification of Nitrospira Species

Primers for use in a diagnostic PCR for the *Nitrospira moscoviensis* clade of FIG. 7 (see Example 2) were designed from aligned sequence datasets (see Tables 3–5 below).

Table 3 is an alignment of 16S rDNA sequences of Nitrospira phylum members and nitrite oxidisers from other bacterial phyla which was used to design the primer MOS457f (SEQ ID NO: 14) for the *Nitrospira mascoviensis* clade. In the table, mismatches with the primer sequence are in bold type and are underlined. The melting temperature calculated for MOS457f (SEQ ID NO:14) was 60° C. and a fragment size of approximately 1052 nucleotides was calculated in a PCR with primer 1492r TACGGYTACCTTGT-TACGACTT (SEQ ID NO:61). The MOS457f (SEQ ID NO:14) sequence corresponds to the sequence at positions 440 to 457 of the *E. coli* 16S rDNA gene.

TABLE 3

| Source of Sequence and Number of Sequence in Sequence Listings | Sequence | Mismatches |
|---|---|---|
| MOS457f primer (SEQ ID NO: 14) | CGGGAGGGAAGATGGAGC | — |
| Nitrococcus mobilis (SEQ ID NO: 17) | CAGCCGGGAGGAAAAGCA | 10 |
| Magnetobacterium bavaricum (SEQ ID NO: 18) | TGTAGGGAAAGATGATGA | 8 |
| Nitrobacter hamburgensis (SEQ ID NO: 19) | TGTGCGGGAAGATAATGA | 7 |
| Nitrospina gracilis (SEQ ID NO: 20) | CGGGTGGGAAGAACAAAA | 6 |
| Nitrospira marina (SEQ ID NO: 21) | CATGAGGAAAGATAAAGT | 6 |
| SBR1015 (SEQ ID NO: 22) | CGGCAGGGAAGATGGAAC | 2 |
| SBR1024 (SEQ ID NO: 22) | CGGCAGGGAAGATGGAAC | 2 |
| SBR2016 (SEQ ID NO: 23) | CGGGAGGGAAGATGGAGC | 0 |
| SBR2046 (SEQ ID NO: 24) | CCGCAGGGAAGATGGAAC | 3 |
| RC7 (SEQ ID NO: 23) | CGGGAGGGAAGATGGAGC | 0 |
| RC11 (SEQ ID NO: 23) | CGGGAGGGAAGATGGAGC | 0 |
| RC14 (SEQ ID NO: 23) | CGGGAGGGAAGATGGAGC | 0 |
| RC19 (SEQ ID NO: 23) | CGGGAGGGAAGATGGAGC | 0 |
| RC25 (SEQ ID NO: 23) | CGGGAGGGAAGATGGAGC | 0 |
| RC73 (SEQ ID NO: 25) | CGGGAGGGAAGATGGAAC | 1 |
| RC90 (SEQ ID NO: 25) | CGGGAGGGAAGATGGAAC | 1 |
| RC99 (SEQ ID NO: 23) | CGGGAGGGAAGATGGAGC | 0 |

TABLE 3-continued

| Source of Sequence and Number of Sequence in Sequence Listings | Sequence | Mismatches |
|---|---|---|
| RC44 (Nitrobacter clone) (SEQ ID NO: 26) | CGTGCGGGAAGATAATGA | 6 |
| GC86 (SEQ ID NO: 27) | CGGCAGGGAAGATGGAAC | 2 |
| Nitrospira miscoviensis (SEQ ID NO: 28) | CGGGAGGGAAGATGGACG | 2 |

Like Table 3, Table 4 is an alignment of 16S rDNA sequences of Nitrospira phylum members and nitrite oxidisers from other bacterial phyla which was used to design the primer MOS638f (SEQ ID NO: 15) for the *Nitrospira moscoviensis* clade. Again, mismatches with the primer sequence are in bold and are underlined. The calculated melting temperature for this primer was 66° C. and a fragment size of approximately 873 nucleotides was calculated in a PCR with primer 1492r TACGGYTACCTTGT-TACGACTT (SEQ ID NO:61). The MOS638f (SEQ ID NO:15) sequence corresponds to the sequence at positions 619 to 638 of the *E. coli* 16S rDNA gene.

Table 5, is again an alignment of 16S rDNA sequences of Nitrospira phylum members and nitrite oxidisers from other bacterial phyla which was used to design the primer MOS635r (SEQ ID NO: 16) for the *Nitrospira moscoviensis* clade. The melting temperature calculated for this primer was 58° C. and a fragment size of approximately 625 nucleotides was calculated in a PCR with primer 27f AGAGTTTGATCCTGGCTCAG (SEQ ID NO:62). The MOS635r (SEQ ID NO:16) sequence corresponds to the sequence at positions 635 to 652 of the *E. coli* 16S rDNA sequence.

TABLE 4

| Source of Sequence and Number of sequence in Sequence Listings | Sequence | Mismatches |
|---|---|---|
| MOS638f primer (SEQ ID NO: 15) | CCAACCCGGAAAGCGCAGAG | — |
| Nitrococcus mobilis (SEQ ID NO: 29) | TCAACCTGGGAATTGCATCC | 8 |
| Magnetobacterium bavaricum (SEQ ID NO: 30) | TCAACCCGGGAATTGCCTTG | 7 |
| Nitrobacter hamburgensis (SEQ ID NO: 31) | TCAACTCCAGAACTGCCTTT | 11 |
| Nitrospina gracilis (SEQ ID NO: 32) | TCAACCGTGGAATTGCGTTT | 10 |
| Nitrospira marina (SEQ ID NO: 33) | TTAACCGGGAAAGGTCGAGA | 9 |
| SBR1015 (SEQ ID NO: 34) | CTAACCCGGAAAGTGCGGAG | 3 |
| SBR1024 (SEQ ID NQ: 34) | CTAACCCGGAAAGTGCGGAG | 3 |
| SBR2016 (SEQ ID NO: 35) | CCAACCCGAAAAGCGCAGAG | 1 |
| SB2046 (SEQ ID NO: 34) | CTAACCCGGAAAGTGCGGAG | 3 |
| RC7 (SEQ ID NO: 36) | CCAACCCGGAAAGCGCAGAG | 0 |
| RC11 (SEQ ID NO: 36) | CCAACCCGGAAAGCGCAGAG | 0 |
| RC14 (SEQ ID NO: 36) | CCAACCCGGAAAGCGCAGAG | 0 |
| RC19 (SEQ ID NO: 36) | CCAACCCGGAAAGCGCAGAG | 0 |
| RC25 (SEQ ID NO: 36) | CCAACCCGGAAAGCGCAGAG | 0 |
| RC73 (SEQ ID NO: 36) | CCAACCCGGAAAGCGCAGAG | 0 |
| RC90 (SEQ ID NO: 36) | CCAACCCGGAAAGCGCAGAG | 0 |
| RC99 (SEQ ID NO: 36) | CCAACCCGGAAAGCGCAGAG | 0 |
| RC44 (Nitrobacter clone) (SEQ ID NO: 37) | TCAACTCCAGAACTGCCTTT | 11 |
| GC86 (SEQ ID NO: 34) | CTAACCCGGAAAGTGCGGAG | 3 |
| Nitrospira moscoviensis (SEQ ID NO: 38) | CCAACCCGGAAAGCGCAGAG | 0 |

TABLE 5

| Source of Sequence and Number of Sequence in Sequence Listings | Sequence | Mismatches |
|---|---|---|
| MOS635r primer (SEQ ID NO: 16) | AGCCTGGCAGTACCCTCT | — |
| *Nitrococcus mobilis* (SEQ ID NO: 39) | AGCCAAACAGTATCGGAT | 7 |
| *Magnetobacterium bavaricum* (SEQ ID NO: 40) | AGTTAAACAGTTTTCAAG | 11 |
| *Nitrobacter hamburgensis* (SEQ ID NO: 41) | AGACCTTCAGTATCAAAG | 9 |
| *Nitrospina gracilis* (SEQ ID NO: 42) | AGCCGAATAGTTTCAAAC | 10 |
| *Nitrospira marina* (SEQ ID NO: 43) | AGCTGAATAGTTCCTCTC | 10 |
| SBR1015 (SEQ ID NO: 44) | AGCCGAGCAGTCCCCTCC | 4 |
| SBR1024 (SEQ ID NO: 44) | AGCCGAGCAGTCCCCTCC | 4 |
| SB2016 (SEQ ID NO: 45) | AGCCTGGCAGTACCCTCT | 0 |
| SB2046 (SEQ ID NO: 44) | AGCCGAGCAGTCCCCTCC | 4 |
| RC7 (SEQ ID NO: 46) | AGCCTGGCAGTACCCCCT | 1 |
| RC11 (SEQ ID NO: 45) | AGCCTGGCAGTACCCTCT | 0 |
| RC14 (SEQ ID NO: 45) | AGCCTGGCAGTACCCTCT | 0 |
| RC19 (SEQ ID NO: 45) | AGCCTGGCAGTACCCTCT | 0 |
| RC25 (SEQ ID NO: 47) | AGCCTGGCAGTACCGTCT | 1 |
| RC73 (SEQ ID NO: 45) | AGCCTGGCAGTACCCTCT | 0 |
| RC90 (SEQ ID NO: 45) | AGCCTGGCAGTACCCTCT | 0 |
| RC99 (SEQ ID NO: 45) | AGCCTGGCAGTACCCTCT | 0 |
| RC44 (Nitrobacter clone) (SEQ ID NO: 48) | AGATCCTCAGTATCAAAG | 10 |
| GC86 (SEQ ID NO: 44) | AGCCGAGCAGTCCCCTCC | 4 |
| *Nitrospira moscoviensis* (SEQ ID NO: 49) | AGCCTGGCAGTACCCTCT | 0 |

The three primers defined above in Tables 3 to 5 were included in separate primer pairs which pairs were then tested in PCR amplifications using genomic DNA from various Nitrospira clones as template. The PCRs were carried out according to methods detailed in Sambrook et al. (1989) at an annealing temperature of 62° C.

Figure 9:
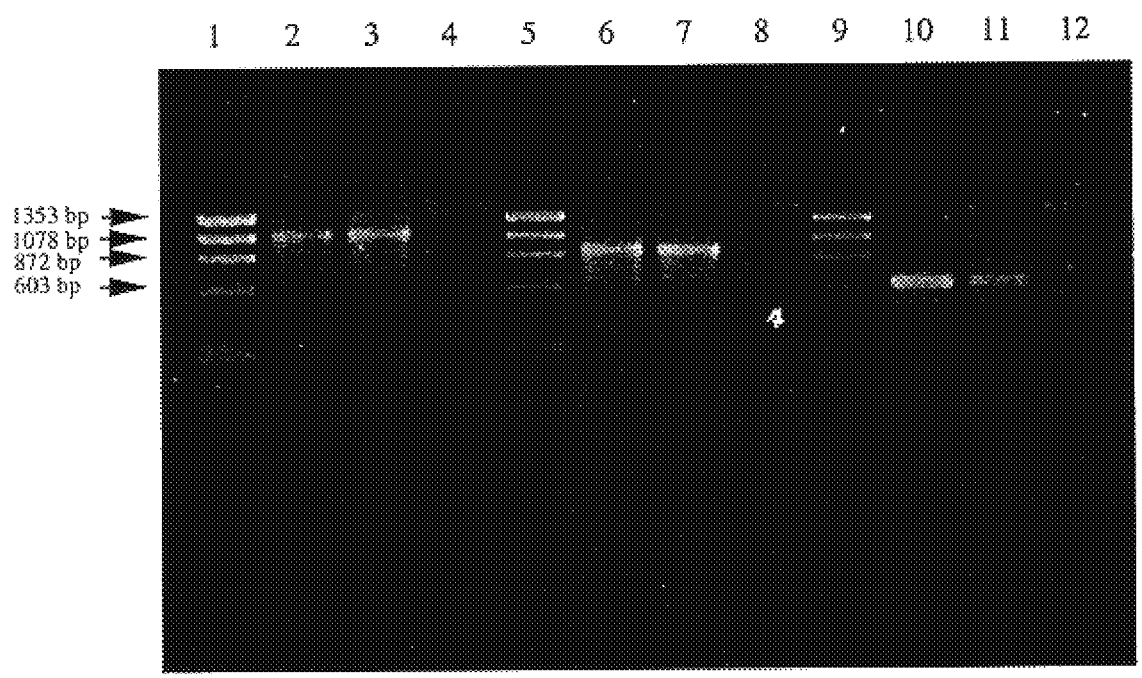
FIG. 9 depicts the results of agarose gel electrophoresis of PCR-amplified DNA using genomic DNA from various Nitrospira clones as template.

The results of electrophoretic analysis of PCRs on an agarose gel are presented in FIG. 9. Details of the material analysed in each lane of the gel are given in Table 6. The marker DNA was HaeIII-digested φX174 DNA. The sizes of the φX174 fragments are given on the left-hand side of the figure.

TABLE 6

| Lane | Primer pair used | Mismatches between primer and template |
|---|---|---|
| 1 | (HaeIII-digested φX174 DNA) | |
| 2 | MOS457f (SEQ ID NO: 14), 1492r (SEQ ID NO: 61) | 0 mismatches with MOS457f |
| 3 | MOS457f, 1492r | 1 mismatch with MOS457f |
| 4 | MOS457f, 1492r | 2 mismatches with MOS457f |
| 5 | (HaeIII-digested φX174 DNA) | |
| 6 | MOS638f (SEQ ID NO: 15), 1492r | 0 mismatches with MOS638f |
| 7 | MOS638f, 1492r | 1 mismatch with MOS638f |
| 8 | MOS638f, 1492r | 3 mismatches with MOS638f |
| 9 | (HaeIII-digested φX174 DNA) | |
| 10 | MOS635r (SEQ ID NO: 16), 27f (SEQ ID NO: 62) | 0 mismatches with MOS635r |
| 11 | MOS635r, 27f | 1 mismatch with MOS635r |
| 12 | MOS635r, 27f | 4 mismatches with MOS635r |

The results presented in FIG. 9 show that an amplicon of the appropriate size was obtained in reactions where there was up to one mismatch between a primer and the template but that no amplicon was produced where there was a greater degree of mismatch.

When the three primer pairs used for the results presented in FIG. 9 were used with clone RC44 (closest match to Nitrobacter), no amplicons were produced.

The primer NIT3 (Wagner et al. 1996; SEQ ID NO: 50) was used in a diagnostic PCR for Nitrobacter. NIT3 (SEQ ID NO:50) was designed originally for fluorescent in situ hybridisation experiments. The specificity of this primer can be appreciated from the sequence alignment presented in Table 7 which is an alignment of 16S rDNA sequences of Nitrospira phylum members and nitrite oxidisers from other bacterial phyla against NIT3 (SEQ ID NO: 50). A melting temperature of 60° C. was calculated for NIT3 (SEQ ID NO: 50) and a fragment size of approximately 1020 nucleotides in a PCR with primer 27f AGAGTTTGATCCTGGCTCAG (SEQ ID NO:62) as experimentally determined. The NIT3 (SEQ ID NO: 50) sequence corresponds to the sequence at positions 1031 to 1048 of the *E.coli* 16S rDNA gene.

TABLE 7

| Source of Sequence and Number of Sequence in Sequence Listings | Sequence | Mismatches |
| --- | --- | --- |
| NIT3 primer (SEQ ID NO: 50) | CCTGTGCTCCATGCTCCG | — |
| *Nitrobacter hamburgensis* (SEQ ID NO: 51) | CCTGTGCTCCATGCTCCG | 0 |
| *Nitrospina gracilis* (SEQ ID NO: 52) | CCTGTGCAAGGGCCCCGA | 9 |
| *Nitrococcus mobilis* (SEQ ID NO: 53) | CCTGTCATCCGGTTCCCG | 7 |
| *Nitrospira moscoviensis* (SEQ ID NO: 54) | CCTGAGCACGCTGGTATT | 8 |
| *Nitrospira marina* (SEQ ID NO: 55) | CCTGAGCTCGCTCCCTT | 7 |
| *Magnetobacterium bavaricum* (SEQ ID NO: 56) | CCTGTGCAAGCTCTCCCT | 8 |
| SBR1015 (SEQ ID NO: 57) | CCTGAGCAGGATGGTATT | 8 |
| SBR1024 (SEQ ID NO: 57) | CCTGAGCAGGATGGTATT | 8 |
| SB2016 (SEQ ID NO: 58) | CCTGAGCACGCTGGTATT | 8 |
| SB2046 (SEQ ID NO: 57) | CCTGAGCAGGATGGTATT | 8 |
| RC7 (SEQ ID NO: 58) | CCTGAGCACGCTGGTATT | 8 |
| RC11 (SEQ ID NO: 58) | CCTGAGCACGCTGGTATT | 8 |
| RC14 (SEQ ID NO: 58) | CCTGAGCACGCTGGTATT | 8 |
| RC19 (SEQ ID NO: 58) | CCTGAGCACGCTGGTATT | 8 |
| RC25 (SEQ ID NO: 58) | CCTGAGCACGCTGGTATT | 8 |
| RC73 (SEQ ID NO: 58) | CCTGAGCACGCTGGTATT | 8 |
| RC90 (SBQ ID NO: 58) | CCTGAGCACGCTGGTATT | 8 |
| GC86 (SEQ ID NO: 59) | CCTGAGCAGGATGGTGTT | 8 |
| RC99 (SEQ ID NO: 58) | CCTGAGCACGCTGGTATT | 8 |

Results of PCRs with the primer pair NIT3 (SEQ ID NO: 50) and 27f (SEQ ID NO: 62) showed that the NIT3 primer specifically amplified only RC44 clone inserts (Nitrobacter) and not those from Nitrospira clones.

The different primer pairs were then used with DNAs extracted from sludges and the results are tabulated below in Table 8. The scorings presented in the table were generated by quantitating by eye the intensity of the amplificate in a stained gel. A definition of the scoring follows: −=no band; +/−=very faint band;+through++++=increasing intensity of the amplificate.

TABLE 8

| Wastewater Treatment Plant | Performance | MOS635r (SEQ ID NO: 16)-27f (SEQ ID NO: 62) 620 bp | NIT3 (SEQ ID NO: 50)-27f (SEQ ID NO: 62) 1020 bp |
|---|---|---|---|
| Oxley | Full nitrification | ++++ | ++ |
| Merrimac | Full nitrification | ++++ | ++ |
| Loganholme | Full nitrification | +++ | +/− |
| Gibson Island | Full nitrification | +++ | − |
| Fairfield | No nitrification | +/− | +++ |
| Cannon Hill | Full nitrification | + | + |
| NOSBR | $NO_2^-$ oxidation | +++++ | ++++ |
| Saline waste water BNR SBR | Partial nitrification | +/− | ++ |
| Nitrifying biofilm reactor | Full nitrification | ++++ | ++++ |
| Phenol/cyanide removing SBR | No nitrification | +/− | ++ |
| BNR SBR | Full nitrification | + | + |

These results show that in plants having good nitrification, Nitraspira species were present as evidenced by amplification of target DNA with the selected primer pairs.

REFERENCES

Blackall, L. L. (1994). Molecular identification of activated sludge foaming bacteria. *Water Science and Technology* 29-7, 35–42.

Blackall, L. L., Seviour, E. M., Cunningham, M. A., Seviour, R. J., and Hugenholtz, P. (1994). "*Microthrix parvicella*" is a novel, deep branching member of the actinomycetes subphylum. *Systematic and Applied Microbiology* 17, 513–518.

Blackburn, T. H. (1983). The Microbial Nitrogen Cycle. In *Microbial Geochemistry*, (pp. 63–89). Edited by W. E. Krumbein. Oxford: Blackwell Scientific Publications.

Bock, E., Koops, H., Ahlers, B., and Harms, H. (1992). Oxidation of inorganic nitrogen compounds as energy source. In *The Prokaryotes—A Handbook on the Biology of Bacteria: Ecophysiology, Isolation, Identification, Applications*, pp. 414–430. Edited by A. Balows, H. G. Trüper, M. Dworkin, W. Harder & K.-H. Schleifer. New York: Springer-Verlag.

Bond, P. L., Hugenholtz, P., Keller, J., and Blackall, L. L. (1995). Bacterial community structures of phosphate-removing and non-phosphate-removing activated sludges from sequencing batch reactors. *Applied and Environmental Microbiology*, 61, 1910–1916.

Burrell, P., and Blackall, L. L. (in press). The microbiology of nitrogen removal in activated sludge systems. In *The Microbiology of Activated Sludge*, Edited by R. J. Seviour & L. L. Blackall.

Ehrich, S., Behrens, D., Lebedeva, E., Ludwig, W. and Bock, E. (1995). A new obligately chemolithoautotrophic, nitrite-oxidizing bacterium, *Nitrospira moscoviensis* sp. nov. and its phylogenetic relationship. *Archives of Microbiology*, 164, 16–23.

Halling-Sørensen, B., and Jørgensen, S. E. (1993). *The Removal of Nitrogen Compounds from Wastewater,* Amsterdam: Elsevier.

Hovanec, T. A. & DeLong, E. F. (1996). Comparative Analysis of Nitrifying Bacteria Associated with Freshwater and Marine Aquaria. *Applied and Environmental Microbiology*, 62, 2888–2896.

Meganck, M. T. J., and Faup, G. M. (1988). Enhanced biological phosphorus removal from waste waters. *Biotreatment Systems*, 3, 111–204.

Randall, C. W. (1992). Introduction and Principles of Biological Nutrient Removal. In *Design and Retrofit of Wastewater Treatment Plants for Biological Nutrient Removal,* (pp. 7–84). Edited by C. W. Randall. Lancaster: Technomic Publishing Company Inc.

Robertson, L. A. & Kuenen, J. G. (1991). Physiology of Nitrifying and Denitrifying Bacteria. In *Microbial Production and Consumption of Greenhouse Gases: Methane, Nitrogen Oxides and Halomethanes,* (pp. 189–199). Edited by J. E. Rogers & W. B. Whitman. Washington D.C.: American Society for Microbiology.

Sambrook, J., Fritsch, E. F., and Maniatis, T., *Molecular Cloning: A Laboratory Manual,* Second Edition, Cold Spring Harbor Laboratory Press, Plainview, N.Y., 1989.

Stackebrandt, E., and Goodfellow, M., eds, *Nucleic Acid Techniques in Bacterial Systematics,* John Wiley & Sons, New York, 1991

Wagner, M., Rath, G., Koops, H.-P., Flood, J., and Amann, R. (1996). In situ analysis of nitrifying bacteria in sewage treatment plants. *Water Science and Technology,* 34, 237–244.

Weidner, S., Arnold, W. and Pühler, A. (1996). Diversity of Uncultured Microorganisms Associated with the seagrass *Halophila stipulacea* Estimated by Restriction Fragment Length Polymorphism Analysis of PCR-Amplified 16S rRNA Genes. *Applied and Environmental Microbiology,* 62, 766–771.

We claim:

1. A primer pair for PCR amplification of Nitrospira DNA, said primer pair comprising:

(a) a first oligonucleotide having the sequence of SEQ ID NO:14 or SEQ ID NO:15; and
   (b) a second oligonucleotide having a sequence of SEQ ID NO:16.

2. A kit comprising, a primer pair according to claim 1,
   wherein said kit further comprises reagents selected from the group consisting of buffers, salts, detergents, nucleotides and thermostable polymerase.

3. A method of detecting a Nitrospira species in a sample, said method comprising the steps of:

(a) lysing cells in said sample to release genomic DNA;
   (b) contacting genomic DNA from step (a) with a primer pair according to claim 1;
   (c) amplifying Nitrospira DNA to produce an amplification product; and
   (d) detecting said amplification product,
   wherein the presence of said product is indicative of the presence of a Nitrospira species in said sample and the absence of said product is indicative of the presence of a Nitrospira species in said sample.

4. A method of quantitating the level of a Nitrospira species in a sample, said method comprising the steps of:

(a) lysing cells in said sample to release genomic DNA;
   (b) contacting genomic DNA from step (a) with a primer pair according to claim 1;
   (c) amplifying Nitrospira DNA to produce an amplification product; and
   (d) detecting said amplification product and quantitating the level of said product by comparison with at least one reference standard,
   wherein the level of said product is indicative of the level of said Nitrospira species.

* * * * *

UNITED STATES PATENT AND TRADEMARK OFFICE
CERTIFICATE OF CORRECTION

PATENT NO. : 6,221,594 B1
DATED : April 24, 2001
INVENTOR(S) : Burrell et al.

It is certified that error appears in the above-identified patent and that said Letters Patent is hereby corrected as shown below:

<u>Column 54, claim 3,</u>
Line 32, "... of the presence of ..." should read -- ... of the absence of ... --

Signed and Sealed this

Nineteenth Day of March, 2002

Attest:

JAMES E. ROGAN
*Director of the United States Patent and Trademark Office*

*Attesting Officer*